United States Patent
Gong et al.

(10) Patent No.: US 11,883,495 B2
(45) Date of Patent: Jan. 30, 2024

(54) ANTI-CD47 ANTIBODIES AND USES THEREOF

(71) Applicant: Lepu Biopharma Co., Ltd., Shanghai (CN)

(72) Inventors: Wenci Gong, Shanghai (CN); Yiwei Tou, Beijing (CN)

(73) Assignee: Lepu Biopharma Co., Ltd., Shanghai (CN)

( * ) Notice: Subject to any disclaimer, the term of this patent is extended or adjusted under 35 U.S.C. 154(b) by 182 days.

(21) Appl. No.: 17/316,152

(22) Filed: May 10, 2021

(65) Prior Publication Data

US 2022/0127357 A1 Apr. 28, 2022

Related U.S. Application Data

(60) Division of application No. 16/999,578, filed on Aug. 21, 2020, now Pat. No. 11,014,984, which is a continuation of application No. PCT/CN2020/096841, filed on Jun. 18, 2020.

(30) Foreign Application Priority Data

Jun. 19, 2019 (WO) ................ PCT/CN2019/091924

(51) Int. Cl.
| | |
|---|---|
| *A61K 39/395* | (2006.01) |
| *C07K 16/30* | (2006.01) |
| *C07K 16/28* | (2006.01) |
| *A61P 35/00* | (2006.01) |
| *G01N 33/68* | (2006.01) |
| *A61K 39/00* | (2006.01) |

(52) U.S. Cl.
CPC ........ *A61K 39/39558* (2013.01); *A61P 35/00* (2018.01); *C07K 16/2803* (2013.01); *G01N 33/6854* (2013.01); *A61K 2039/505* (2013.01); *C07K 2317/24* (2013.01); *C07K 2317/31* (2013.01); *C07K 2317/565* (2013.01); *C07K 2317/76* (2013.01); *C07K 2317/92* (2013.01)

(58) Field of Classification Search
CPC .......................... C07K 16/30; A61K 39/39558
See application file for complete search history.

(56) References Cited

U.S. PATENT DOCUMENTS

| | | | |
|---|---|---|---|
| 8,562,997 B2 | 10/2013 | Jaiswal et al. | |
| 9,796,781 B2 | 10/2017 | Majeti et al. | |
| 2006/0115832 A1* | 6/2006 | Hoon | C12Q 1/6886 435/6.16 |
| 2008/0280297 A1* | 11/2008 | Dalla-Favera | G01N 33/57426 435/6.16 |
| 2011/0190157 A1* | 8/2011 | Kipps | C12Q 1/6809 506/17 |
| 2012/0178111 A1* | 7/2012 | Diamandis | G01N 33/57423 435/7.1 |
| 2014/0140989 A1 | 5/2014 | Eckelman et al. | |
| 2014/0161799 A1 | 6/2014 | Frazier et al. | |

FOREIGN PATENT DOCUMENTS

| | | |
|---|---|---|
| CN | 103665165 | 3/2014 |
| EP | 1693385 | 8/2006 |
| WO | WO 2015/191861 | 12/2015 |
| WO | WO 2018/195302 A1 | 10/2018 |
| WO | WO 2019/034895 A1 | 2/2019 |
| WO | WO 2019/042285 A1 | 3/2019 |
| WO | WO 2019/095358 A1 | 5/2019 |
| WO | WO 2019/108733 A2 | 6/2019 |

OTHER PUBLICATIONS

Evans et Al. (Q. J. Med 1999: 92: 299-307) (Year: 1999).*
Schiffman et Al. (The New England Journal of Medicine, Vo. 353, No. 20, p. 2101-2104, 2005) (Year: 2005).*
Cuzick et Al. (The Lancet, vol. 361, p. 296-300, 2003) (Year: 2003).*
Hernandez-Ledesma (Peptides, vol. 30, p. 426-430, 2009) (Year: 2009).*
Baxevanis (Expert Opinion: Drug Discovery, vol. 3, No. 4, p. 441-452, 2008) (Year: 2008).*
Polyak et Al. (Blood, vol. 99, No. 9, p. 3256-3262, 2002) (Year: 2002).*
Munodzana et Al. (Infection and Immunity, vol. 66 No. 6, p. 2619-2624, 1998) (Year: 1998).*
Komenaka et Al., Clinics in Dermatology, 2004, vol. 22, p. 251-265 (Year: 2004).*
International Search Report and Written Opinion dated Sep. 10, 2020 for PCT/CN2020/096841. (15 pages).
Paul. Structure and Function of Immunoglobulins. Fundamental Immunology, 3$^{rd}$ Edition. 1993; 292-295.
Rudikoff, et al. Single amino acid substitution altering antigen-binding specificity. Proc. Natl. Acad. Sci. USA. Mar. 1986; 79:1979-1983.

* cited by examiner

*Primary Examiner* — Michael Allen

(74) *Attorney, Agent, or Firm* — Sheppard Mullin Richter & Hampton LLP

(57) ABSTRACT

Provided are anti-CD47 antibodies and fragments thereof. The antibodies and fragments thereof specifically bind to the CD47 protein. Methods of using the antibodies or fragments thereof for treating and diagnosing diseases such as cancer and atherosclerosis are also provided.

8 Claims, 7 Drawing Sheets
Specification includes a Sequence Listing.

ANTI-CD47 ANTIBODIES AND USES THEREOF

CROSS REFERENCE TO RELATED APPLICATIONS

This application is a division of U.S. application Ser. No. 16/999,578 filed on Aug. 21, 2020, which is a continuation of International Application No. PCT/CN2020/096841, filed Jun. 18, 2020, which claims priority to International Application No. PCT/CN2019/091924, filed Jun. 19, 2019. The contents of each of the aforementioned are hereby incorporated by reference in their entirety into the present disclosure.

SEQUENCE LISTING

The instant application contains a Sequence Listing which has been filed electronically in ASCII format and is hereby incorporated by reference in its entirety. Said ASCII copy, created on Aug. 20, 2020, is named 298467US_ST25.txt and is 13,516 bytes in size.

BACKGROUND

CD47 (Cluster of Differentiation 47) protein, also known as integrin associated protein (IAP), is a 50 kDa transmembrane protein that belongs to the immunoglobulin superfamily CD47 partners with membrane integrins and also binds to the ligands thrombospondin-1 (TSP-1) and signal-regulatory protein alpha (SIRP-α). CD47 is involved in a range of cellular processes, including apoptosis, proliferation, adhesion, and migration. Furthermore, it plays a key role in immune and angiogenic responses. CD47 is ubiquitously expressed in human cells and has been found to be overexpressed in many different tumor cells.

CD47 was first identified as a tumor antigen on human ovarian cancer. Since then, CD47 has been found to be expressed on multiple human tumor types including acute myeloid leukemia (AML), chronic myeloid leukemia, acute lymphoblastic leukemia (ALL), non-Hodgkin's lymphoma (NHL), multiple myeloma (MM), bladder cancer, and other solid tumors. High levels of CD47 allows cancer cells to avoid phagocytosis despite having a higher level of calreticulin, the dominant pro-phagocytic signal. This is due to engagement of the SIRP-α of macrophage by CD47. Engagement of SIRP-α leads to inhibition of phagocytosis. Therefore, blocking CD47 triggers the recognition and elimination of cancer cells by the innate immunity, and favors phagocytosis.

Anti-CD47 antibody treatment not only enables macrophage phagocytosis of cancer, but also fosters the activation of cancer-specific lymphocytes. Anti-CD47 antibodies are being evaluated for the treatment of various cancers, e.g., relapsed/refractory B-cell non-Hodgkin's lymphoma, solid tumors, colorectal cancer, ovarian cancer, diffuse large B-cell lymphoma (DLBCL) and follicular lymphoma (FL).

SUMMARY

The present disclosure provides anti-CD47 antibodies having high binding affinity to human CD47 proteins and can effectively block the interaction between CD47 and its receptor SIRP-α. The examples provided herein demonstrate that the anti-CD47 antibodies disclosed herein promote phagocytosis of tumor cells by human MΦ. Meanwhile, unlike a reference anti-CD47 antibody that showed significant RBC agglutination, the present antibodies caused essentially no RBC agglutination at the tested concentrations up to 150 μg/mL. These anti-CD47 antibodies are useful for therapeutic purposes such as treating various types of cancer and can also be used for diagnostic and prognostic purposes.

Some embodiments provide an antibody or fragment thereof, wherein the antibody or fragment thereof has specificity to a human CD47 (Cluster of Differentiation 47) protein and comprises: (a) a VH CDR1 comprising the amino acid sequence of SEQ ID NO: 1 or a variant of SEQ ID NO: 1 having a single substitution, deletion or insertion from SEQ ID NO: 1; (b) a VH CDR2 comprising the amino acid sequence of SEQ ID NO: 2 or SEQ ID NO: 7, or a variant of SEQ ID NO: 2 or SEQ ID NO: 7 having a single substitution, deletion or insertion at position 4, 7, 12, or 15 of SEQ ID NO: 2 or SEQ ID NO: 7; (c) a VH CDR3 comprising the amino acid sequence of SEQ ID NO: 3 or SEQ ID NO: 8, or a variant of SEQ ID NO: 3 or SEQ ID NO: 8 having a single substitution, deletion or insertion at position 1 or 2 of SEQ ID NO: 3 or SEQ ID NO: 8; (d) a VL CDR1 comprising the amino acid sequence of SEQ ID NO: 4 or SEQ ID NO: 9, or a variant of SEQ ID NO: 4 or SEQ ID NO: 9 having a single substitution, deletion or insertion at position 1 or 6 of SEQ ID NO: 4 or SEQ ID NO: 9; (e) a VL CDR2 comprising the amino acid sequence of SEQ ID NO: 5 or a variant of SEQ ID NO: 5 having a single substitution, deletion or insertion from SEQ ID NO: 5; and (f) a VL CDR3 comprising the amino acid sequence of SEQ ID NO: 6 or SEQ ID NO: 10, or a variant of SEQ ID NO: 6 or SEQ ID NO: 10 having a single substitution, deletion or insertion at position 5 of SEQ ID NO: 6 or SEQ ID NO: 10.

In some embodiments, the antibody or fragment thereof comprises a VH CDR1 of SEQ ID NO: 1, a VH CDR2 of SEQ ID NO: 2, a VH CDR3 of SEQ ID NO: 3, a VL CDR1 of SEQ ID NO: 4, a VL CDR2 of SEQ ID NO: 5, and a VL CDR3 of SEQ ID NO: 6.

Examples of such antibodies and fragments include those having a heavy chain variable region comprising an amino acid sequence selected from the group consisting of SEQ ID NOs: 11 and 15-16, or a peptide having at least 90% sequence identity to an amino acid sequence selected from the group consisting of SEQ ID NOs: 11 and 15-16. Examples of such antibodies and fragments include those having a light chain variable region comprising an amino acid sequence selected from the group consisting of SEQ ID NOs: 12 and 17, or a peptide having at least 90% sequence identity to an amino acid sequence selected from the group consisting of SEQ ID NO: 12 and 17.

In some examples, the antibody or fragment thereof comprises a heavy chain variable region comprising the amino acid sequence of SEQ ID NO:15 or 16 or a peptide having at least 90% sequence identity to the amino acid sequence of SEQ ID NO:15 or 16, and a light chain variable region comprising the amino acid sequence of SEQ ID NO:17 or a peptide having at least 90% sequence identity to the amino acid sequence of SEQ ID NO:17.

In some embodiments, the antibody or fragment thereof comprises a VH CDR1 of SEQ ID NO: 1, a VH CDR2 of SEQ ID NO: 7, a VH CDR3 of SEQ ID NO: 8, a VL CDR1 of SEQ ID NO: 9, a VL CDR2 of SEQ ID NO: 5, and a VL CDR3 of SEQ ID NO: 10.

Examples of such antibodies and fragments include those having a heavy chain variable region comprising an amino acid sequence selected from the group consisting of SEQ ID NOs: 13 and 18-19, or a peptide having at least 90% sequence identity to an amino acid sequence selected from the group consisting of SEQ ID NOs: 13 and 18-19. Examples of such antibodies and fragments include those a light chain variable region comprising an amino acid sequence selected from the group consisting of SEQ ID NOs: 14 and 20, or a peptide having at least 90% sequence identity to an amino acid sequence selected from the group consisting of SEQ ID NO: 14 and 20.

In some embodiments, the antibody or fragment thereof comprises a heavy chain variable region comprising the amino acid sequence of SEQ ID NO:18 or 19 or a peptide having at least 90% sequence identity to the amino acid sequence of SEQ ID NO:18 or 19, and a light chain variable region comprising the amino acid sequence of SEQ ID NO:20 or a peptide having at least 90% sequence identity to the amino acid sequence of SEQ ID NO:20.

The antibody or fragment thereof disclosed herein can further comprises a heavy chain constant region, a light chain constant region, an Fc region, or the combination thereof. The light chain constant region, for example, can be a kappa or lambda chain constant region.

In some embodiments, the antibody or fragment thereof is of an isotype of IgG, IgM, IgA, IgE or IgD. In some embodiments, the isotype is IgG1, IgG2, IgG3 or IgG4.

The antibody or fragment thereof can be, for example, a chimeric antibody, a humanized antibody, or a fully human antibody. In some embodiments, the antibody or fragment thereof is a humanized antibody.

In some embodiments, the antibody or fragment thereof comprises a heavy chain variable region comprising one or more amino acid residues selected from the group consisting of: (a) Ile at position 2, (b) Val at position 71, (c) Thr at position 76, and (d) Thr at position 93, according to Kabat numbering, and combinations thereof.

Provided herein includes a composition comprising at least one of the antibodies or fragments thereof disclosed herein and a pharmaceutically acceptable carrier. Also disclosed includes an isolated cell comprising one or more polynucleotides encoding at least one of the antibodies or fragments thereof.

A method of treating cancer in a patient in need thereof is also provided, where the method comprises administering to the patient an effective amount of at least one of the antibodies or fragments thereof disclosed herein. The cancer can be a solid tumor or a hematologic malignancy. In some embodiments, the cancer is bladder cancer, liver cancer, colon cancer, rectal cancer, endometrial cancer, leukemia, lymphoma, pancreatic cancer, small cell lung cancer, non-small cell lung cancer, breast cancer, urethral cancer, head and neck cancer, gastrointestinal cancer, stomach cancer, oesophageal cancer, ovarian cancer, renal cancer, melanoma, prostate cancer, thyroid cancer, or a combination thereof. In some embodiments, the method further comprises administering to the patient a second cancer therapeutic agent.

Also provided herein is a method of detecting expression of CD47 in a sample, comprising contacting the sample with at least one of the antibodies or fragments thereof disclosed herein under conditions for the antibody or fragment thereof to bind to the CD47, and detecting the binding which indicates expression of CD47 in the sample. The sample can comprise a tumor cell, a tumor tissue, a blood sample, or a combination thereof.

Some embodiments provide an isolated bispecific antibody comprising a fragment of the anti-CD47 antibody disclosed herein and a second antigen-binding fragment having specificity to a molecule on an immune cell. The molecule on the immune cell can be, for example, PD-L1, PD-1, CTLA-4, LAG-3, CD28, CD122, 4-1BB, TIM3, OX-40, OX40L, CD40, CD40L, LIGHT, ICOS, ICOSL, GITR, GITRL, TIGIT, CD27, VISTA, B7H3, B7H4, HEVM, BTLA, or KIR. In some embodiments, the fragment and the second antigen-binding fragment each is independently selected from a Fab fragment, a single-chain variable fragment (scFv), or a single-domain antibody. In some embodiments, the bispecific antibody further comprises a Fc fragment.

Some embodiments provide compositions and methods for treating an autoimmune or inflammatory disease such as, without limitation, atherosclerosis.

DETAILED DESCRIPTION

Definitions

Figure 1:
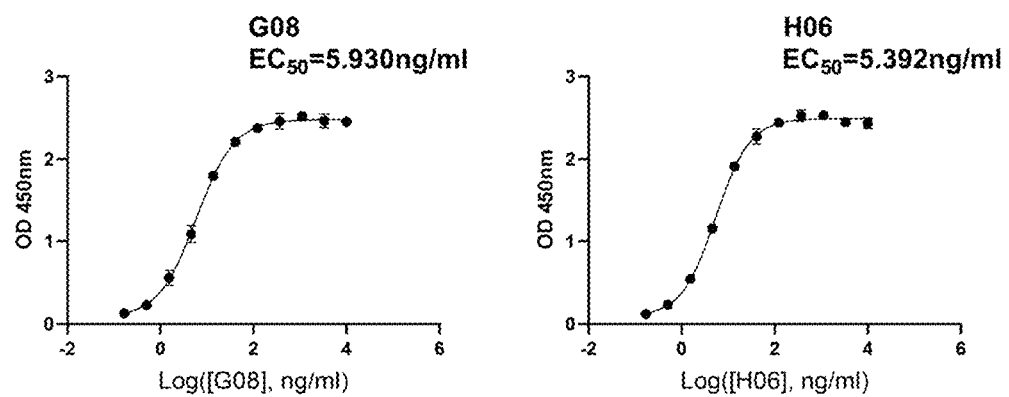
FIG. 1 shows that G08 and H06 antibodies bind to human CD47 in a dose-dependent manner.

It is to be noted that the term "a" or "an" entity refers to one or more of that entity; for example, "an antibody," is understood to represent one or more antibodies. As such, the terms "a" (or "an"), "one or more," and "at least one" can be used interchangeably herein.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

The term "isolated" as used herein with respect to cells, proteins, nucleic acids (such as DNA or RNA, refers to molecules separated from other DNAs or RNAs), respectively, that are present in the natural source of the macromolecule. The term "isolated" as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to cells or polypeptides which are isolated from other cellular proteins or tissues. Isolated polypeptides is meant to encompass both purified and recombinant polypeptides.

As used herein, the term "recombinant" as it pertains to polypeptides or polynucleotides intends a form of the polypeptide or polynucleotide that does not exist naturally, a non-limiting example of which can be created by combining polynucleotides or polypeptides that would not normally occur together.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present disclosure.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology. In some embodiments, default parameters are used for alignment. One non-limiting alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by =HIGH SCORE; Databases=non-redundant, GenBank+EMBL+DDBJ+PDB+GenBank CDS translations+SwissProtein+SPupdate+PIR. Biologically equivalent polynucleotides are those having the above-noted specified percent homology and encoding a polypeptide having the same or similar biological activity.

As used herein, the term "an equivalent nucleic acid or polynucleotide" refers to a nucleic acid having a nucleotide sequence having a certain degree of homology, or sequence identity, with the nucleotide sequence of the nucleic acid or complement thereof. A homolog of a double stranded nucleic acid is intended to include nucleic acids having a nucleotide sequence which has a certain degree of homology with or with the complement thereof. In one aspect, homologs of nucleic acids are capable of hybridizing to the nucleic acid or complement thereof. Likewise, "an equivalent polypeptide" refers to a polypeptide having a certain degree of homology, or sequence identity, with the amino acid sequence of a reference polypeptide. In some aspects, the sequence identity is at least about 70%, 75%, 80%, 85%, 90%, 95%, 98%, or 99%. In some aspects, the equivalent polypeptide or polynucleotide has one, two, three, four or five addition, deletion, substitution and their combinations thereof as compared to the reference polypeptide or polynucleotide. In some aspects, the equivalent sequence retains the activity (e.g., epitope-binding) or structure (e.g., salt-bridge) of the reference sequence.

Hybridization reactions can be performed under conditions of different "stringency". In general, a low stringency hybridization reaction is carried out at about 40° C. in about 10×SSC or a solution of equivalent ionic strength/temperature. A moderate stringency hybridization is typically performed at about 50° C. in about 6×SSC, and a high stringency hybridization reaction is generally performed at about 60° C. in about 1×SSC. Hybridization reactions can also be performed under "physiological conditions" which is well known to one of skill in the art. A non-limiting example of a physiological condition is the temperature, ionic strength, pH and concentration of $Mg^{2+}$ normally found in a cell.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching. The term "polymorphism" refers to the coexistence of more than one form of a gene or portion thereof. A portion of a gene of which there are at least two different forms, i.e., two different nucleotide sequences, is referred to as a "polymorphic region of a gene". A polymorphic region can be a single nucleotide, the identity of which differs in different alleles.

As used herein, the terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. Non-limiting examples of polynucleotide include: a gene or gene fragment (for example, a probe, primer, EST or SAGE tag), exons, introns, messenger RNA (mRNA), transfer RNA, ribosomal RNA, ribozymes, cDNA, dsRNA, siRNA, miRNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this disclosure that is a polynucleotide encompasses both the double-stranded form and each of two complementary single-stranded forms known or predicted to make up the double-stranded form.

As used herein, the term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

As used herein, an "antibody" or "antigen-binding polypeptide" refers to a polypeptide or a polypeptide complex that specifically recognizes and binds to an antigen. An antibody can be a whole antibody and any antigen binding fragment or a single chain thereof. Thus the term "antibody" includes any protein or peptide containing molecule that comprises at least a portion of an immunoglobulin molecule having biological activity of binding to the antigen. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein.

The terms "antibody fragment" or "antigen-binding fragment", as used herein, is a portion of an antibody such as F(ab')$_2$, F(ab)$_2$, Fab', Fab, Fv, scFv and the like. Regardless of structure, an antibody fragment binds with the same antigen that is recognized by the intact antibody. The term "antibody fragment" includes aptamers, Spiegelmer™ L-ribonucleic acid aptamers, and diabodies. The term "antibody fragment" also includes any synthetic or genetically engineered protein that acts like an antibody by binding to a specific antigen to form a complex.

As used herein, a "single-chain variable fragment" or "scFv" refers to a fusion protein of the variable regions of the heavy ($V_H$) and light chains ($V_L$) of immunoglobulins. In some embodiments, the regions are connected with a short linker peptide of ten to about 25 amino acids. The linker can be rich in glycine for flexibility, as well as serine or threonine for solubility, and can either connect the N-terminus of the $V_H$ with the C-terminus of the $V_L$, or vice versa. This protein retains the specificity of the original immunoglobulin, despite removal of the constant regions and the introduction of the linker. ScFv molecules are known in the art and are described, e.g., in U.S. Pat. No. 5,892,019.

As used herein, the term "antibody" encompasses various broad classes of polypeptides that can be distinguished biochemically. Those of skill in the art will appreciate that heavy chains are classified as gamma, mu, alpha, delta, or epsilon (γ, μ, α, δ, or ε) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., IgG$_1$, IgG$_2$, IgG$_3$, IgG$_4$, IgG$_5$, etc. are well characterized and are known to confer functional specialization. Modified versions of each of these classes and isotypes are readily discernable to the skilled artisan in view of the instant disclosure and, accordingly, are within the scope of the instant disclosure. All immunoglobulin classes are clearly within the scope of the present disclosure, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight approximately 53,000-70,000 Daltons. The four chains are typically joined by disulfide bonds in a "Y" configuration wherein the light chains bracket the heavy chains starting at the mouth of the "Y" and continuing through the variable region.

Antibodies, antigen-binding polypeptides, variants, or derivatives thereof of the disclosure include, but are not limited to, polyclonal, monoclonal, multispecific, human, humanized, primatized, or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a VK or VH domain, fragments produced by a Fab expression library, and anti-idiotypic (anti-Id) antibodies (including, e.g., anti-Id antibodies to LIGHT antibodies disclosed herein) Immunoglobulin or antibody molecules of the disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

Light chains are classified as either kappa or lambda (K, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VK) and heavy (VH) chain portions determine antigen recognition and specificity. Conversely, the constant domains of the light chain (CK) and the heavy chain (CH1, CH2 or CH3) confer important biological properties such as secretion, transplacental mobility, Fc receptor binding, complement binding, and the like. By convention the numbering of the constant region domains increases as they become more distal from the antigen-binding site or amino-terminus of the antibody. The N-terminal portion is a variable region and at the C-terminal portion is a constant region; the CH3 and CK domains actually comprise the carboxy-terminus of the heavy and light chain, respectively.

As indicated above, the variable region allows the antibody to selectively recognize and specifically bind epitopes on antigens. That is, the VK domain and VH domain, or subset of the complementarity determining regions (CDRs), of an antibody combine to form the variable region that defines a three dimensional antigen-binding site. This quaternary antibody structure forms the antigen-binding site present at the end of each arm of the Y. More specifically, the antigen-binding site is defined by three CDRs on each of the VH and VK chains (i.e. CDR-H1, CDR-H2, CDR-H3, CDR-L1, CDR-L2 and CDR-L3). In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., Nature 363:446-448 (1993).

In naturally occurring antibodies, the six "complementarity determining regions" or "CDRs" present in each antigen-binding domain are short, non-contiguous sequences of amino acids that are specifically positioned to form the antigen-binding domain as the antibody assumes its three dimensional configuration in an aqueous environment. The remainder of the amino acids in the antigen-binding domains, referred to as "framework" regions, show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see "Sequences of Proteins of Immunological Interest," Kabat, E., et al., U.S. Department of Health and Human Services, (1983); and Chothia and Lesk, J. Mol. Biol., 196:901-917 (1987)).

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., J. Mol. Biol. 196:901-917 (1987), which are incorporated herein by reference in their entireties. The CDR definitions according to Kabat and Chothia include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth in the table below as a comparison. The exact residue numbers which encompass a particular CDR will vary depending on the sequence and size of the CDR. Those of skill in the art can routinely determine which residues comprise a particular CDR given the variable region amino acid sequence of the antibody.

|        | Kabat  | Chothia |
|--------|--------|---------|
| CDR-H1 | 31-35  | 26-32   |
| CDR-H2 | 50-65  | 52-58   |
| CDR-H3 | 95-102 | 95-102  |
| CDR-L1 | 24-34  | 26-32   |
| CDR-L2 | 50-56  | 50-52   |
| CDR-L3 | 89-97  | 91-96   |

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983).

In addition to table above, the Kabat number system describes the CDR regions as follows: CDR-H1 begins at approximately amino acid 31 (i.e., approximately 9 residues after the first cysteine residue), includes approximately 5-7 amino acids, and ends at the next tryptophan residue. CDR-H2 begins at the fifteenth residue after the end of CDR-H1, includes approximately 16-19 amino acids, and ends at the next arginine or lysine residue. CDR-H3 begins at approximately the thirty third amino acid residue after the end of CDR-H2; includes 3-25 amino acids. CDR-L1 begins at approximately residue 24 (i.e., following a cysteine residue); includes approximately 10-17 residues; and ends at the next tryptophan residue. CDR-L2 begins at approximately the sixteenth residue after the end of CDR-L1 and includes approximately 7 residues. CDR-L3 begins at approximately the thirty third residue after the end of CDR-L2 (i.e., following a cysteine residue); includes approximately 7-11 residues.

Antibodies disclosed herein can be from any animal origin including birds and mammals. Preferably, the antibodies are human, murine, donkey, rabbit, goat, guinea pig, camel, llama, horse, or chicken antibodies. In some embodiments, the variable region may be condricthoid in origin (e.g., from sharks).

As used herein, the term "heavy chain constant region" includes amino acid sequences derived from an immunoglobulin heavy chain. A polypeptide comprising a heavy chain constant region comprises at least one of: a CH1 domain, a hinge (e.g., upper, middle, and/or lower hinge region) domain, a CH2 domain, a CH3 domain, or a variant or fragment thereof. For example, an antigen-binding polypeptide for use in the disclosure may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the disclosure comprises a polypeptide chain comprising a CH3 domain. Further, an antibody for use in the disclosure may lack at least a portion of a CH2 domain (e.g., all or part of a CH2 domain). As set forth above, it will be understood by one of skill in the art that the heavy chain constant region may be modified such that they vary in amino acid sequence from the naturally occurring immunoglobulin molecule.

The heavy chain constant region of an antibody disclosed herein may be derived from different immunoglobulin molecules. For example, a heavy chain constant region of a polypeptide may comprise a CH1 domain derived from an $IgG_1$ molecule and a hinge region derived from an $IgG_3$ molecule. In another example, a heavy chain constant region can comprise a hinge region derived, in part, from an IgG1 molecule and, in part, from an $IgG_3$ molecule. In another example, a heavy chain portion can comprise a chimeric hinge derived, in part, from an $IgG_1$ molecule and, in part, from an $IgG_4$ molecule.

As used herein, the term "light chain constant region" includes amino acid sequences derived from antibody light chain. Preferably, the light chain constant region comprises at least one of a constant kappa domain or constant lambda domain.

A "light chain-heavy chain pair" refers to the collection of a light chain and heavy chain that can form a dimer through a disulfide bond between the CL domain of the light chain and the CH1 domain of the heavy chain.

As previously indicated, the subunit structures and three dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat et al., U.S. Dept. of Health and Human Services, "Sequences of Proteins of Immunological Interest" (1983). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains (Roux et al., *J. Immunol* 161:4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CK regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" will be held to mean any antibody wherein the immunoreactive region or site is obtained or derived from a first species and the constant region (which may be intact, partial or modified in accordance with the instant disclosure) is obtained from a second species. In certain embodiments the target binding region or site will be from a non-human source (e.g. mouse or primate) and the constant region is human.

As used herein, "percent humanization" is calculated by determining the number of framework amino acid differences (i.e., non-CDR difference) between the humanized domain and the germline domain, subtracting that number from the total number of amino acids, and then dividing that by the total number of amino acids and multiplying by 100.

By "specifically binds" or "has specificity to," it is generally meant that an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

As used herein, the terms "treat" or "treatment" refer to both therapeutic treatment and prophylactic or preventative measures, wherein the object is to prevent or slow down (lessen) an undesired physiological change or disorder, such as the progression of cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sport, or pet animals such as dogs, cats, guinea pigs, rabbits, rats, mice, horses, cattle, cows, and so on.

As used herein, phrases such as "to a patient in need of treatment" or "a subject in need of treatment" includes subjects, such as mammalian subjects (including human subject), that would benefit from administration of an antibody or composition of the present disclosure used, e.g., for detection, for a diagnostic procedure and/or for treatment.

Anti-CD47 Antibodies

The present disclosure provides anti-CD47 antibodies with high affinity to the human CD47 protein and can effectively block the interaction between CD47 and its receptor SIRP-α. Also, these anti-CD47 antibodies promote phagocytosis of tumor cells by human MΦ. Yet another significant advantage of the presently disclosed antibodies, as compared to certain known anti-CD47 antibodies, is that these antibodies do not cause RBC agglutination even at high concentrations. The tested antibodies exhibited potent binding and inhibitory activities and are useful for therapeutic and diagnostics uses.

The CD47 protein is a 50 kDa transmembrane protein that has extracellular N-terminal IgV domain, five transmembrane domains, and a short C-terminal intracellular tail. CD47 has been shown to be a ligand for SIRP-α which belong to the Ig family of cell surface glycoproteins, and a receptor for Thrombospondin-1 (TSP-1), the prototypic member of the thrombospondin family of extracellular matrix glycoproteins. The CD47/SIRP-α interaction regulates not only a multitude of intercellular interactions in many body systems, such as the immune system where it regulates lymphocyte homeostasis, dendritic cell (DC) maturation and activation, proper localization of certain DC subsets in secondary lymphoid organs, and cellular transmigration, but also regulates cells of the nervous system. An interaction between CD47 and SIRP-α also plays an important role in bone remodeling.

Some embodiments provide anti-CD47 antibodies comprising heavy chain and light chain variable domains with the CDR regions as defined in SEQ ID NO: 1-6. Some embodiments provide anti-CD47 antibodies comprising heavy chain and light chain variable domains with the CDR regions as defined in SEQ ID NO:1, 7-9, 5 and 10.

TABLE 1

Sequences of the CDR regions

| Name | Sequence | SEQ ID NO: |
|---|---|---|
| G08 VH CDR1 | DYYIN | 1 |
| G08 VH CDR2 | WIYTGSGNTKYNEKFKG | 2 |
| G08 VH CDR3 | YNPLITAVVPDY | 3 |

TABLE 1-continued

Sequences of the CDR regions

| Name | Sequence | SEQ ID NO: |
|---|---|---|
| G08 VL CDR1 | KSSQSLLYSSNQKNYLA | 4 |
| G08 VL CDR2 | WASTRES | 5 |
| G08 VL CDR3 | QQYYSYPPT | 6 |
| H06 VH CDR1 | DYYIN | 1 |
| H06 VH CDR2 | WIPGSANTKYSEKVKG | 7 |
| H06 VH CDR3 | NDPLITAVVPDY | 8 |
| H06 VL CDR1 | RSSQSRLYSSNQKNYLA | 9 |
| H06 VL CDR2 | WASTRES | 5 |
| H06 VL CDR3 | QQYYNYPPT | 10 |

Certain amino acid locations in Table 1 are highlighted, which have different amino acids between antibodies B08 and H06. These suggest that amino acids at these locations can vary without reducing the antigen binding affinity or other biological activity of the antibody.

As demonstrated in the experimental examples disclosed herein, the antibodies that contain CDR regions defined in SEQ ID NOs: 1-6 or CDR regions defined in SEQ ID NOs: 1, 7-9, 5 and 10, whether mouse or humanized had potent CD47 binding and inhibitory activities. In some embodiments, an anti-CD47 antibody of the present disclosure includes one or more of the VH and VL CDRs as listed in Table 1, with one, two or three modifications. Such modifications can be addition, deletion or substation of amino acids. In some embodiments, at least one of the modifications is at one of the amino acid positions that are underlined and bold in Table 1. For example, the modification can be at any position of SEQ ID NO: 1 or 5; position 4, 7, 12, and/or 15 of SEQ ID NO: 2 or SEQ ID NO: 7; position 1 and/or 2 of SEQ ID NO: 3 or SEQ ID NO: 8; position 1 or 6 of SEQ ID NO: 4 or SEQ ID NO: 9; position 5 of SEQ ID NO: 6 or SEQ ID NO: 10; or any combination thereof.

In some embodiments, the isolated anti-CD47 antibody or fragment thereof comprises: (a) a VH CDR1 of SEQ ID NO: 1, or a variant of SEQ ID NO: 1 having a single substitution, deletion or insertion; (b) a VH CDR2 of SEQ ID NO: 2, or a variant of SEQ ID NO: 2 having a single, double, triple or quadruple substitution, deletion or insertion at position 4, 7, 12, and/or 15 of SEQ ID NO: 2; (c) a VH CDR3 of SEQ ID NO: 3, or a variant of SEQ ID NO: 3 having a single or double substitution, deletion or insertion at position 1 and/or 2 of SEQ ID NO: 3; (d) a VL CDR1 of SEQ ID NO: 4, or a variant of SEQ ID NO: 4 having a single substitution, deletion or insertion at position 1 or 6 of SEQ ID NO: 4; (e) a VL CDR2 of SEQ ID NO: 5 or a variant of SEQ ID NO: 5 having a single substitution, deletion or insertion; and (f) a VL CDR3 of SEQ ID NO: 6, or a variant of SEQ ID NO: 6 having a single substitution, deletion or insertion at position 5 of SEQ ID NO: 6.

In some embodiments, the isolated anti-CD47 antibody or fragment thereof comprises: (a) a VH CDR1 of SEQ ID NO: 1; (b) a VH CDR2 of SEQ ID NO: 2; (c) a VH CDR3 of SEQ ID NO: 3; (d) a VL CDR1 of SEQ ID NO: 4; (e) a VL CDR2 of SEQ ID NO: 5; and (f) a VL CDR3 of SEQ ID NO: 6. In some embodiments, the isolated anti-CD47 antibody or fragment thereof comprises: (a) a VH CDR1 of SEQ ID NO: 1, or a variant of SEQ ID NO: 1 having at least 75%, 80%, 85%, 90%, 95%, 98%, or 99% sequence identity to SEQ ID NO: 1; (b) a VH CDR2 of SEQ ID NO: 2, or a variant of SEQ ID NO: 2 having at least 75%, 80%, 85%, 90%, 95%, 98%, or 99% sequence identity to SEQ ID NO: 2; (c) a VH CDR3 of SEQ ID NO: 3, or a variant of SEQ ID NO: 3 having at least 75%, 80%, 85%, 90%, 95%, 98%, or 99% sequence identity to SEQ ID NO: 3; (d) a VL CDR1 of SEQ ID NO: 4, or a variant of SEQ ID NO: 4 having at least 75%, 80%, 85%, 90%, 95%, 98%, or 99% sequence identity to SEQ ID NO: 4; (e) a VL CDR2 of SEQ ID NO: 5; and (f) a VL CDR3 of SEQ ID NO: 6, or a variant of SEQ ID NO: 6 having at least 75%, 80%, 85%, 90%, 95%, 98%, or 99% sequence identity to SEQ ID NO: 6.

In some embodiments, the isolated anti-CD47 antibody or fragment thereof comprises: (a) a VH CDR1 of SEQ ID NO: 1, or a variant of SEQ ID NO: 1 having a single substitution, deletion or insertion relative to SEQ ID NO: 1; (b) a VH CDR2 of SEQ ID NO: 2, or a variant of SEQ ID NO: 2 having a single substitution, deletion or insertion relative to SEQ ID NO: 2; (c) a VH CDR3 of SEQ ID NO: 3, or a variant of SEQ ID NO: 3 having a single substitution, deletion or insertion relative to SEQ ID NO: 3; (d) a VL CDR1 of SEQ ID NO: 4, or a variant of SEQ ID NO: 4 having a single substitution, deletion or insertion relative to SEQ ID NO: 4; (e) a VL CDR2 of SEQ ID NO: 5, or a variant of SEQ ID NO: 5 having a single substitution, deletion or insertion relative to SEQ ID NO: 5; and (f) a VL CDR3 of SEQ ID NO: 6, or a variant of SEQ ID NO: 6 having a single substitution, deletion or insertion relative to SEQ ID NO: 6.

In some embodiments, the isolated anti-CD47 antibody or fragment thereof comprises: (a) a VH CDR1 of SEQ ID NO: 1, or a variant of SEQ ID NO: 1 having a single substitution, deletion or insertion; (b) a VH CDR2 of SEQ ID NO: 7, or a variant of SEQ ID NO: 7 having a single, double, triple or quadruple substitution, deletion or insertion at position 4, 7, 12, and/or 15 of SEQ ID NO: 7; (c) a VH CDR3 of SEQ ID NO: 8, or a variant of SEQ ID NO: 8 having a single or double substitution, deletion or insertion at position 1 and/or 2 of SEQ ID NO: 8; (d) a VL CDR1 of SEQ ID NO: 9, or a variant of SEQ ID NO: 9 having a single substitution, deletion or insertion at position 1 or 6 of SEQ ID NO: 9; (e) a VL CDR2 of SEQ ID NO: 5, or a variant of SEQ ID NO: 5 having a single substitution, deletion or insertion; and (f) a VL CDR3 of SEQ ID NO: 10, or a variant of SEQ ID NO: 10 having a single substitution, deletion or insertion at position 5 of SEQ ID NO: 10.

In some embodiments, the isolated anti-CD47 antibody or fragment thereof comprises: (a) a VH CDR1 of SEQ ID NO: 1; (b) a VH CDR2 of SEQ ID NO: 7; (c) a VH CDR3 of SEQ ID NO: 8; (d) a VL CDR1 of SEQ ID NO: 9; (e) a VL CDR2 of SEQ ID NO: 5; and (f) a VL CDR3 of SEQ ID NO: 10.

In some embodiments, the isolated anti-CD47 antibody or fragment thereof comprises: (a) a VH CDR1 of SEQ ID NO: 1, or a variant of SEQ ID NO: 1 having at least 75%, 80%, 85%, 90%, 95%, 98%, or 99% sequence identity to SEQ ID NO: 1; (b) a VH CDR2 of SEQ ID NO: 7, or a variant of SEQ ID NO: 7 having at least 75%, 80%, 85%, 90%, 95%, 98%, or 99% sequence identity to SEQ ID NO: 7; (c) a VH CDR3 of SEQ ID NO: 8, or a variant of SEQ ID NO: 8 having at least 75%, 80%, 85%, 90%, 95%, 98%, or 99% sequence identity to SEQ ID NO: 8; (d) a VL CDR1 of SEQ ID NO: 9, or a variant of SEQ ID NO: 9 having at least 75%, 80%, 85%, 90%, 95%, 98%, or 99% sequence identity to SEQ ID NO: 9; (e) a VL CDR2 of SEQ ID NO: 5 or a variant of SEQ ID NO: 5 having at least 75%, 80%, 85%, 90%, 95%, 98%, or 99% sequence identity to SEQ ID NO:5; and (f) a VL CDR3 of SEQ ID NO: 10, or a variant of SEQ ID NO:10 having at least 75%, 80%, 85%, 90%, 95%, 98%, or 99% sequence identity to SEQ ID NO: 10.

In some embodiments, the isolated anti-CD47 antibody or fragment thereof comprises: (a) a VH CDR1 of SEQ ID NO: 1, or a variant of SEQ ID NO: 1 having a single substitution, deletion or insertion relative to SEQ ID NO: 1; (b) a VH CDR2 of SEQ ID NO: 7, or a variant of SEQ ID NO: 7 having a single substitution, deletion or insertion relative to SEQ ID NO: 7; (c) a VH CDR3 of SEQ ID NO: 8, or a variant of SEQ ID NO: 8 having a single substitution, deletion or insertion relative to SEQ ID NO: 8; (d) a VL CDR1 of SEQ ID NO: 9, or a variant of SEQ ID NO: 9 having a single substitution, deletion or insertion relative to SEQ ID NO: 9; (e) a VL CDR2 of SEQ ID NO: 5, or a variant of SEQ ID NO: 5 having a single substitution, deletion or insertion relative to SEQ ID NO: 5; and (f) a VL CDR3 of SEQ ID NO: 10, or a variant of SEQ ID NO: 10 having a single substitution, deletion or insertion relative to SEQ ID NO: 10.

The substitutions disclosed herein, in some embodiments, are conservative substitutions.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in an immunoglobulin polypeptide is preferably replaced with another amino acid residue from the same side chain family. In another embodiment, a string of amino acids can be replaced with a structurally similar string that differs in order and/or composition of side chain family members.

Non-limiting examples of conservative amino acid substitutions are provided in Tables 2-3, where a similarity score of 0 or higher (see Table 2) indicates conservative substitution between the two amino acids.

TABLE 2

Amino Acid Similarity Matrix

| | C | G | P | S | A | T | D | E | N | Q | H | K | R | V | M | I | L | F | Y | W |
|---|---|---|---|---|---|---|---|---|---|---|---|---|---|---|---|---|---|---|---|---|
| W | −8 | −7 | −6 | −2 | −6 | −5 | −7 | −7 | −4 | −5 | −3 | −3 | 2 | −6 | −4 | −5 | −2 | 0 | 0 | 17 |
| Y | 0 | −5 | −5 | −3 | −3 | −3 | −4 | −4 | −2 | −4 | 0 | −4 | −5 | −2 | −2 | −1 | −1 | 7 | 10 | |
| F | −4 | −5 | −5 | −3 | −4 | −3 | −6 | −5 | −4 | −5 | −2 | −5 | −4 | −1 | 0 | 1 | 2 | 9 | | |
| L | −6 | −4 | −3 | −3 | −2 | −2 | −4 | −3 | −3 | −2 | −2 | −3 | −3 | 2 | 4 | 2 | 6 | | | |
| I | −2 | −3 | −2 | −1 | −1 | 0 | −2 | −2 | −2 | −2 | −2 | −2 | −2 | 4 | 2 | 5 | | | | |
| M | −5 | −3 | −2 | −2 | −1 | −1 | −3 | −2 | 0 | −1 | −2 | 0 | 0 | 2 | 6 | | | | | |
| V | −2 | −1 | −1 | −1 | 0 | 0 | −2 | −2 | −2 | −2 | −2 | −2 | −2 | 4 | | | | | | |
| R | −4 | −3 | 0 | 0 | −2 | −1 | −1 | −1 | 0 | 1 | 2 | 3 | 6 | | | | | | | |
| K | −5 | −2 | −1 | 0 | −1 | 0 | 0 | 0 | 1 | 1 | 0 | 5 | | | | | | | | |
| H | −3 | −2 | 0 | −1 | −1 | −1 | 1 | 1 | 2 | 3 | 6 | | | | | | | | | |
| Q | −5 | −1 | 0 | −1 | 0 | −1 | 2 | 2 | 1 | 4 | | | | | | | | | | |
| N | −4 | 0 | −1 | 1 | 0 | 0 | 2 | 1 | 2 | | | | | | | | | | | |
| E | −5 | 0 | −1 | 0 | 0 | 0 | 3 | 4 | | | | | | | | | | | | |
| D | −5 | 1 | −1 | 0 | 0 | 0 | 4 | | | | | | | | | | | | | |
| T | −2 | 0 | 0 | 1 | 1 | 3 | | | | | | | | | | | | | | |
| A | −2 | 1 | 1 | 1 | 2 | | | | | | | | | | | | | | | |
| S | 0 | 1 | 1 | 1 | | | | | | | | | | | | | | | | |
| P | −3 | −1 | 6 | | | | | | | | | | | | | | | | | |
| G | −3 | 5 | | | | | | | | | | | | | | | | | | |
| C | 12 | | | | | | | | | | | | | | | | | | | |

TABLE 3

Conservative Amino Acid Substitutions

| For Amino Acid | Substitution With |
|---|---|
| Alanine | D-Ala, Gly, Aib, β-Ala, L-Cys, D-Cys |
| Arginine | D-Arg, Lys, D-Lys, Orn D-Orn |
| Asparagine | D-Asn, Asp, D-Asp, Glu, D-Glu Gln, D-Gln |
| Aspartic Acid | D-Asp, D-Asn, Asn, Glu, D-Glu, Gln, D-Gln |
| Cysteine | D-Cys, S-Me-Cys, Met, D-Met, Thr, D-Thr, L-Ser, D-Ser |
| Glutamine | D-Gln, Asn, D-Asn, Glu, D-Glu, Asp, D-Asp |
| Glutamic Acid | D-Glu, D-Asp, Asp, Asn, D-Asn, Gln, D-Gln |
| Glycine | Ala, D-Ala, Pro, D-Pro, Aib, β-Ala |
| Isoleucine | D-Ile, Val, D-Val, Leu, D-Leu, Met, D-Met |
| Leucine | Val, D-Val, Met, D-Met, D-Ile, D-Leu, Ile |
| Lysine | D-Lys, Arg, D-Arg, Orn, D-Orn |
| Methionine | D-Met, S-Me-Cys, Ile, D-Ile, Leu, D-Leu, Val, D-Val |

TABLE 3-continued

Conservative Amino Acid Substitutions

| For Amino Acid | Substitution With |
|---|---|
| Phenylalanine | D-Phe, Tyr, D-Tyr, His, D-His, Trp, D-Trp |
| Proline | D-Pro |
| Serine | D-Ser, Thr, D-Thr, allo-Thr, L-Cys, D-Cys |
| Threonine | D-Thr, Ser, D-Ser, allo-Thr, Met, D-Met, Val, D-Val |
| Tyrosine | D-Tyr, Phe, D-Phe, His, D-His, Trp, D-Trp |
| Valine | D-Val, Leu, D-Leu, Ile, D-Ile, Met, D-Met |

In some embodiments, the substitution is with an amino acid at the same CDR position from another antibody of the present disclosure. For instance, the T4 of SEQ ID NO:2 can be substituted with P, the G7 of SEQ ID NO:2 can be substituted with A, the N12 of SEQ ID NO:2 can be substituted with S, the F15 of SEQ ID NO:2 can be substituted with V, the Y1 of SEQ ID NO:3 can be substituted with N, the N2 of SEQ ID NO:3 can be substituted with D, the K1 of SEQ ID NO:4 can be substituted with R, the L6 of SEQ ID NO:4 can be substituted with R, the S5 of SEQ ID NO:6 can be substituted with N, the P4 of SEQ ID NO:7 can be substituted with T, the A7 of SEQ ID NO:7 can be substituted with G, the S12 of SEQ ID NO:7 can be substituted with N, the V15 of SEQ ID NO:7 can be substituted with F, the N1 of SEQ ID NO:8 can be substituted with Y, the D2 of SEQ ID NO:8 can be substituted with N, the R1 of SEQ ID NO:9 can be substituted with K, the R6 of SEQ ID NO:9 can be substituted with L, the N5 of SEQ ID NO:10 can be substituted with S.

Examples of antibodies and fragments include those having a heavy chain variable region comprising an amino acid sequence selected from the group consisting of SEQ ID NOs: 11 and 15-16, or a peptide having at least 75%, 80%, 85%, 90%, 95%, 98%, or 99% sequence identity to an amino acid sequence selected from the group consisting of SEQ ID NOs: 11 and 15-16. Examples of such antibodies and fragments include those having a light chain variable region comprising an amino acid sequence selected from the group consisting of SEQ ID NOs: 12 and 17, or a peptide having at least 75%, 80%, 85%, 90%, 95%, 98%, or 99% sequence identity to an amino acid sequence selected from the group consisting of SEQ ID NO: 12 and 17.

In some examples, the antibody or fragment thereof comprises a heavy chain variable region comprising the amino acid sequence of SEQ ID NO:15 or 16 or a peptide having at least 75%, 80%, 85%, 90%, 95%, 98%, or 99% sequence identity to the amino acid sequence of SEQ ID NO:15 or 16, and a light chain variable region comprising the amino acid sequence of SEQ ID NO:17 or a peptide having at least 75%, 80%, 85%, 90%, 95%, 98%, or 99% sequence identity to the amino acid sequence of SEQ ID NO:17.

Examples of antibodies and fragments also include those a heavy chain variable region comprising an amino acid sequence selected from the group consisting of SEQ ID NOs: 13 and 18-19, or a peptide having at least 75%, 80%, 85%, 90%, 95%, 98%, or 99% sequence identity to an amino acid sequence selected from the group consisting of SEQ ID NOs: 13 and 18-19. Examples of such antibodies and fragments include those a light chain variable region comprising an amino acid sequence selected from the group consisting of SEQ ID NOs: 14 and 20, or a peptide having at least 75%, 80%, 85%, 90%, 95%, 98%, or 99% sequence identity to an amino acid sequence selected from the group consisting of SEQ ID NO: 14 and 20.

In some embodiments, the antibody or fragment thereof comprises a heavy chain variable region comprising the amino acid sequence of SEQ ID NO:18 or 19 or a peptide having at least 75%, 80%, 85%, 90%, 95%, 98%, or 99% sequence identity to the amino acid sequence of SEQ ID NO:18 or 19, and a light chain variable region comprising the amino acid sequence of SEQ ID NO:20 or a peptide having at least 75%, 80%, 85%, 90%, 95%, 98%, or 99% sequence identity to the amino acid sequence of SEQ ID NO:20.

Among the humanized VH, SEQ ID NO: 16 includes one or more back-mutations to the mouse version. Likewise, a non-limiting example of VL is provided in SEQ ID NO: 19 with back-mutations.

In some embodiments, back-mutations can be useful for retaining one or more characteristics of the anti-CD47 antibodies. Accordingly, in some embodiments, the anti-CD47 antibodies of the present disclosure, in particular the human or humanized ones, include one or more of the back-mutations. In some embodiments, the VH back-mutation (i.e., included amino acid at the specified position) is one or more selected from (a) Ile at position 2, (b) Val at position 71, (c) Thr at position 76, and (d) Thr at position 93, according to Kabat numbering, and combinations thereof. In some embodiments, the back-mutations are selected from (a) Ile at position 2 and (b) Val at position 71, according to Kabat numbering, and combinations thereof.

It will also be understood by one of skill in the art that antibodies as disclosed herein may be modified such that they vary in amino acid sequence from the naturally occurring binding polypeptide from which they were derived. For example, a polypeptide or amino acid sequence derived from a designated protein may be similar, e.g., have a certain percent identity to the starting sequence, e.g., it may be 60%, 70%, 75%, 80%, 85%, 90%, 95%, 98%, 99%, or a range between any two of these values, identical to the starting sequence.

In some embodiments, the antibody comprises an amino acid sequence or one or more moieties not normally associated with an antibody. Exemplary modifications are described in more detail herein. For example, an antibody disclosed herein may comprise a flexible linker sequence, or may be modified to add a functional moiety (e.g., PEG, a drug, a toxin, or a label).

Antibodies, variants, or derivatives thereof of the disclosure include derivatives that are modified, i.e., by the covalent attachment of any type of molecule to the antibody such that covalent attachment does not prevent the antibody from binding to the epitope. For example, but not by way of limitation, the antibodies can be modified, e.g., by glycosylation, acetylation, pegylation, phosphorylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the antibodies may contain one or more non-classical amino acids.

In some embodiments, the antibodies may be conjugated to therapeutic agents, prodrugs, peptides, proteins, enzymes, viruses, lipids, biological response modifiers, pharmaceutical agents, or PEG.

The antibodies may be conjugated or fused to a therapeutic agent, which may include detectable labels such as radioactive labels, an immunomodulator, a hormone, an enzyme, an oligonucleotide, a photoactive therapeutic or diagnostic agent, a cytotoxic agent, which may be a drug or a toxin, an ultrasound enhancing agent, a non-radioactive label, a combination thereof and other such agents known in the art.

The antibodies can be detectably labeled by coupling it to a chemiluminescent compound. The presence of the chemiluminescent-tagged antigen-binding polypeptide is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

The antibodies can also be detectably labeled using fluorescence emitting metals such as 152m, r, or others of the lanthanide series. These metals can be attached to the antibody using such metal chelating groups as diethylenetriaminepentacetic acid (DTPA) or ethylenediaminetetraacetic acid (EDTA). Techniques for conjugating various moieties to an antibody are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. (1985); Hellstrom et al., "Antibodies For Drug Delivery", in Controlled Drug Delivery (2nd Ed.), Robinson et al., (eds.), Marcel Dekker, Inc., pp. 623-53 (1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), Academic Press pp. 303-16 (1985), and Thorpe et al., "The Preparation And Cytotoxic Properties Of Antibody-Toxin Conjugates", *Immunol. Rev.* (52:119-58 (1982)).

Bi-Functional Molecules

CD47 is a tumor antigen. As a tumor antigen targeting molecule, an antibody or antigen-binding fragment specific to CD47 can be combined with a second antigen-binding fragment specific to an immune cell to generate a bispecific antibody.

In some embodiments, the immune cell is selected from the group consisting of a T cell, a B cell, a monocyte, a macrophage, a neutrophil, a dendritic cell, a phagocyte, a natural killer cell, an eosinophil, a basophil, and a mast cell. Molecules on the immune cell which can be targeted include, for example, CD3, CD16, CD19, CD28, and CD64. Other examples include PD-1, CTLA-4, LAG-3 (also known as CD223), CD28, CD122, 4-1BB (also known as CD137), TIN/13, OX-40 or OX40L, CD40 or CD40L, LIGHT, ICOS/ICOSL, GITR/GITRL, TIGIT, CD27, VISTA, B7H3, B7H4, HEVM or BTLA (also known as CD272), and killer-cell immunoglobulin-like receptors (KIRs). Specific examples of bispecificity include, without limitation, CD47/LAG3, CD47/TIGIT, CD47/PD-1, and CD47/PD-L1.

As disclosed herein, an antibody or antigen-binding fragment specific to CD47 can be combined with a second antigen-binding fragment specific to a tumor antigen to generate a bispecific antibody. A "tumor antigen" refers to an antigenic substance produced in tumor cells, i.e., it triggers an immune response in the host. Tumor antigens are useful in identifying tumor cells and are potential candidates for use in cancer therapy. Normal proteins in the body are not antigenic. Certain proteins, however, are produced or overexpressed during tumorigenesis and thus appear "foreign" to the body. This may include normal proteins that are well sequestered from the immune system, proteins that are normally produced in extremely small quantities, proteins that are normally produced only in certain stages of development, or proteins whose structure is modified due to mutation.

An abundance of tumor antigens are known in the art and new tumor antigens can be readily identified by screening. Non-limiting examples of tumor antigens include EGFR, Her2, EpCAM, CD20, CD30, CD33, CD47, CD52, CD133, CD73, CEA, gpA33, Mucins, TAG-72, CIX, PSMA, folate-binding protein, GD2, GD3, GM2, VEGF, VEGFR, Integrin, $\alpha V\beta 3$, $\alpha 5\beta 1$, ERBB2, ERBB3, MET, IGF1R, EPHA3, TRAILR1, TRAILR2, RANKL, FAP and Tenascin.

In some aspects, the monovalent unit has specificity to a protein that is overexpressed on a tumor cell as compared to a corresponding non-tumor cell. A "corresponding non-tumor cell" as used here, refers to a non-tumor cell that is of the same cell type as the origin of the tumor cell. It is noted that such proteins are not necessarily different from tumor antigens. Non-limiting examples include carcinoembryonic antigen (CEA), which is overexpressed in most colon, rectum, breast, lung, pancreas and gastrointestinal tract carcinomas; heregulin receptors (HER-2, neu or c-erbB-2), which is frequently overexpressed in breast, ovarian, colon, lung, prostate and cervical cancers; epidermal growth factor receptor (EGFR), which is highly expressed in a range of solid tumors including those of the breast, head and neck, non-small cell lung and prostate; asialoglycoprotein receptor; transferrin receptor; serpin enzyme complex receptor, which is expressed on hepatocytes; fibroblast growth factor receptor (FGFR), which is overexpressed on pancreatic ductal adenocarcinoma cells; vascular endothelial growth factor receptor (VEGFR), for anti-angiogenesis gene therapy; folate receptor, which is selectively overexpressed in 90% of nonmucinous ovarian carcinomas; cell surface glycocalyx; carbohydrate receptors; and polymeric immunoglobulin receptor, which is useful for gene delivery to respiratory epithelial cells and attractive for treatment of lung diseases such as Cystic Fibrosis. Non-limiting examples of bispecificity in this respect include CD47/EGFR, CD47/Her2, CD47/CD33, CD47/CD133, CD47/CEA and CD47/VEGF.

Different format of bispecific antibodies are also provided. In some embodiments, each of the anti-CD47 fragment and the second fragment each is independently selected from a Fab fragment, a single-chain variable fragment (scFv), or a single-domain antibody. In some embodiments, the bispecific antibody further includes a Fc fragment.

Bifunctional molecules that include not just antibody or antigen binding fragment are also provided. As a tumor antigen targeting molecule, an antibody or antigen-binding fragment specific to CD47, such as those described here, can be combined with an immune cytokine or ligand optionally through a peptide linker. The linked immune cytokines or ligands include, but not limited to, IL-2, IL-3, IL-4, IL-5, IL-6, IL-7, IL-10, IL-12, IL-13, IL-15, GM-CSF, TNF-α, CD40L, OX40L, CD27L, CD30L, 4-1BBL, LIGHT and GITRL. Such bi-functional molecules can combine the immune checkpoint blocking effect with tumor site local immune modulation.

Polynucleotides Encoding the Antibodies and Methods of Preparing the Antibodies

The present disclosure also provides isolated polynucleotides or nucleic acid molecules encoding the antibodies, variants or derivatives thereof of the disclosure. The polynucleotides of the present disclosure may encode the entire heavy and light chain variable regions of the antigen-binding polypeptides, variants or derivatives thereof on the same polynucleotide molecule or on separate polynucleotide molecules. Additionally, the polynucleotides of the present disclosure may encode portions of the heavy and light chain variable regions of the antigen-binding polypeptides, variants or derivatives thereof on the same polynucleotide molecule or on separate polynucleotide molecules.

Methods of making antibodies are well known in the art and described herein. In certain embodiments, both the variable and constant regions of the antigen-binding polypeptides of the present disclosure are fully human Fully human antibodies can be made using techniques described in the art and as described herein. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make such antibodies are described in U.S. Pat. Nos. 6,150,584; 6,458,592; 6,420,140 which are incorporated by reference in their entireties.

In certain embodiments, the prepared antibodies will not elicit a deleterious immune response in the animal to be treated, e.g., in a human. In one embodiment, antigen-binding polypeptides, variants, or derivatives thereof of the disclosure are modified to reduce their immunogenicity using art-recognized techniques. For example, antibodies can be humanized, primatized, deimmunized, or chimeric antibodies can be made. These types of antibodies are derived from a non-human antibody, typically a murine or primate antibody, that retains or substantially retains the antigen-binding properties of the parent antibody, but which is less immunogenic in humans. This may be achieved by various methods, including (a) grafting the entire non-human variable domains onto human constant regions to generate chimeric antibodies; (b) grafting at least a part of one or more of the non-human complementarity determining regions (CDRs) into a human framework and constant regions with or without retention of critical framework residues; or (c) transplanting the entire non-human variable domains, but "cloaking" them with a human-like section by replacement of surface residues. Such methods are disclosed in Morrison et al., *Proc. Natl. Acad. Sci. USA* 57:6851-6855 (1984); Morrison et al., *Adv. Immunol.* 44:65-92 (1988); Verhoeyen et al., *Science* 239:1534-1536 (1988); Padlan, *Molec. Immun.* 25:489-498 (1991); Padlan, *Molec. Immun.* 31:169-217 (1994), and U.S. Pat. Nos. 5,585,089, 5,693,761, 5,693,762, and 6,190,370, all of which are hereby incorporated by reference in their entirety.

De-immunization can also be used to decrease the immunogenicity of an antibody. As used herein, the term "de-immunization" includes alteration of an antibody to modify T-cell epitopes (see, e.g., International Application Publication Nos.: WO/9852976 A1 and WO/0034317 A2). For example, variable heavy chain and variable light chain sequences from the starting antibody are analyzed and a human T-cell epitope "map" from each V region showing the location of epitopes in relation to complementarity-determining regions (CDRs) and other key residues within the sequence is created. Individual T-cell epitopes from the T-cell epitope map are analyzed in order to identify alternative amino acid substitutions with a low risk of altering activity of the final antibody. A range of alternative variable heavy and variable light sequences are designed comprising combinations of amino acid substitutions and these sequences are subsequently incorporated into a range of binding polypeptides. Typically, between 12 and 24 variant antibodies are generated and tested for binding and/or function. Complete heavy and light chain genes comprising modified variable and human constant regions are then cloned into expression vectors and the subsequent plasmids introduced into cell lines for the production of whole antibody. The antibodies are then compared in appropriate biochemical and biological assays, and the optimal variant is identified.

The binding specificity of antigen-binding polypeptides of the present disclosure can be determined by in vitro assays such as immunoprecipitation, radioimmunoassay (RIA) or enzyme-linked immunoabsorbent assay (ELISA).

Alternatively, techniques described for the production of single-chain units (U.S. Pat. No. 4,694,778; Bird, *Science* 242:423-442 (1988); Huston et al., *Proc. Natl. Acad. Sci. USA* 55:5879-5883 (1988); and Ward et al., *Nature* 334:544-554 (1989)) can be adapted to produce single-chain units of the present disclosure. Single-chain units are formed by linking the heavy and light chain fragments of the Fv region via an amino acid bridge, resulting in a single-chain fusion peptide. Techniques for the assembly of functional Fv fragments in *E. coli* may also be used (Skerra et al., *Science* 242:1038-1041 (1988)).

Examples of techniques which can be used to produce single-chain Fvs (scFvs) and antibodies include those described in U.S. Pat. Nos. 4,946,778 and 5,258,498; Huston et al., *Methods in Enzymology* 203:46-88 (1991); Shu et al., *Proc. Natl. Sci. USA* 90:1995-1999 (1993); and Skerra et al., *Science* 240:1038-1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See, e.g., Morrison, *Science* 229:1202 (1985); Oi et al., *BioTechniques* 4:214 (1986); Gillies et al., *J. Immunol. Methods* 125:191-202 (1989); U.S. Pat. Nos. 5,807,715; 4,816,567; and 4,816397, which are incorporated herein by reference in their entireties.

Humanized antibodies are antibody molecules derived from a non-human species antibody that bind the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen-binding. These framework substitutions are identified by methods well known in the art, e.g., by modeling of the interactions of the CDR and framework residues to identify framework residues important for antigen-binding and sequence comparison to identify unusual framework residues at particular positions. (See, e.g., Queen et al., U.S. Pat. No. 5,585,089; Riechmann et al., *Nature* 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, *Molecular Immunology* 28(4/5):489-498 (1991); Studnicka et al., *Protein Engineering* 7(6):805-814 (1994); Roguska. et al., *Proc. Natl. Sci. USA* 91:969-973 (1994)), and chain shuffling (U.S. Pat. No. 5,565,332, which is incorporated by reference in its entirety).

Completely human antibodies are particularly desirable for therapeutic treatment of human patients. Human antibodies can be made by a variety of methods known in the art including phage display methods using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a desired target polypeptide. Monoclonal antibodies directed against the antigen can be obtained from the immunized, transgenic mice using conventional hybridoma technology. The human immunoglobulin transgenes harbored by the transgenic mice rearrange during B-cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar *Int. Rev. Immunol.* 73:65-93 (1995). For a detailed discussion of this technology for producing human antibodies and human monoclonal antibodies and protocols for producing such antibodies, see, e.g., PCT publications WO 98/24893; WO 96/34096; WO 96/33735; U.S. Pat. Nos. 5,413,923; 5,625,126; 5,633,425; 5,569,825; 5,661,016; 5,545,806; 5,814,318; and 5,939,598, which are incorporated by reference herein in their entirety. In addition, companies such as Abgenix, Inc. (Freemont, Calif.) and GenPharm (San Jose, Calif.) can be engaged to provide human antibodies directed against a selected antigen using technology similar to that described above.

Completely human antibodies which recognize a selected epitope can also be generated using a technique referred to as "guided selection." In this approach a selected non-human monoclonal antibody, e.g., a mouse antibody, is used to guide the selection of a completely human antibody recognizing the same epitope. (Jespers et al., *Bio/Technology* 72:899-903 (1988). See also, U.S. Pat. No. 5,565,332, which is incorporated by reference in its entirety.)

DNA encoding desired monoclonal antibodies can be readily isolated and sequenced using conventional procedures (e.g., by using oligonucleotide probes that are capable of binding specifically to genes encoding the heavy and light chains of murine antibodies). The isolated and subcloned hybridoma cells serve as a preferred source of such DNA. Once isolated, the DNA may be placed into expression vectors, which are then transfected into prokaryotic or eukaryotic host cells such as *E. coli* cells, simian COS cells, Chinese Hamster Ovary (CHO) cells or myeloma cells that do not otherwise produce immunoglobulins. More particularly, the isolated DNA (which may be synthetic as described herein) may be used to clone constant and variable region sequences for the manufacture antibodies as described in Newman et al., U.S. Pat. No. 5,658,570, filed Jan. 25, 1995, which is incorporated by reference herein. Essentially, this entails extraction of RNA from the selected cells, conversion to cDNA, and amplification by PCR using Ig specific primers. Suitable primers for this purpose are also described in U.S. Pat. No. 5,658,570. As described herein, transformed cells expressing the desired antibody can be grown up in relatively large quantities to provide clinical and commercial supplies of the immunoglobulin.

Additionally, using routine recombinant DNA techniques, one or more of the CDRs of the antigen-binding polypeptides of the present disclosure, may be inserted within framework regions, e.g., into human framework regions to humanize a non-human antibody. The framework regions may be naturally occurring or consensus framework regions, and preferably human framework regions (see, e.g., Chothia et al., *J. Mol. Biol.* 278:457-479 (1998) for a listing of human framework regions). Preferably, the polynucleotide generated by the combination of the framework regions and CDRs encodes an antibody that specifically binds to at least one epitope of a desired polypeptide, e.g., LIGHT. Preferably, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present disclosure and within the skill of the art.

In addition, techniques developed for the production of "chimeric antibodies" (Morrison et al., *Proc. Natl. Acad. Sci. USA*:851-855 (1984); Neuberger et al., *Nature* 372:604-608 (1984); Takeda et al., *Nature* 314:452-454 (1985)) by splicing genes from a mouse antibody molecule, of appropriate antigen specificity, together with genes from a human antibody molecule of appropriate biological activity can be used. As used herein, a chimeric antibody is a molecule in which different portions are derived from different animal species, such as those having a variable region derived from a murine monoclonal antibody and a human immunoglobulin constant region.

Yet another highly efficient means for generating recombinant antibodies is disclosed by Newman, *Biotechnology* 10: 1455-1460 (1992). Specifically, this technique results in the generation of primatized antibodies that contain monkey variable domains and human constant sequences. This reference is incorporated by reference in its entirety herein. Moreover, this technique is also described in commonly assigned U.S. Pat. Nos. 5,658,570, 5,693,780 and 5,756,096 each of which is incorporated herein by reference.

Alternatively, antibody-producing cell lines may be selected and cultured using techniques well known to the skilled artisan. Such techniques are described in a variety of laboratory manuals and primary publications. In this respect, techniques suitable for use in the disclosure as described below are described in *Current Protocols in Immunology*, Coligan et al., Eds., Green Publishing Associates and Wiley-Interscience, John Wiley and Sons, New York (1991) which is herein incorporated by reference in its entirety, including supplements.

Additionally, standard techniques known to those of skill in the art can be used to introduce mutations in the nucleotide sequence encoding an antibody of the present disclosure, including, but not limited to, site-directed mutagenesis and PCR-mediated mutagenesis which result in amino acid substitutions. Preferably, the variants (including derivatives) encode fewer than 50 amino acid substitutions, fewer than 40 amino acid substitutions, fewer than 30 amino acid substitutions, fewer than 25 amino acid substitutions, fewer than 20 amino acid substitutions, fewer than 15 amino acid substitutions, fewer than 10 amino acid substitutions, fewer than 5 amino acid substitutions, fewer than 4 amino acid substitutions, fewer than 3 amino acid substitutions, or fewer than 2 amino acid substitutions relative to the reference variable heavy chain region, CDR-H1, CDR-H2, CDR-H3, variable light chain region, CDR-L1, CDR-L2, and/or CDR-L3. In some embodiments, one or more mutations are introduced randomly along all or part of the coding sequence, such as by saturation mutagenesis, and the resultant mutants can be screened for biological activity to identify mutants that retain activity.

Treatments

The anti-CD47 antibodies, variants or derivatives disclosed herein be used in treatment and diagnostic methods, for example for treating and/or diagnosing cancers.

The present disclosure includes antibody-based therapies which comprise administering the antibodies, variants, derivatives, or fragments thereof of the disclosure to a patient such as an animal, a mammal, and a human for treating one or more of the disorders or conditions described herein. Therapeutic compounds of the disclosure include, but are not limited to, antibodies of the disclosure (including variants and derivatives thereof as described herein), nucleic acids or polynucleotides encoding antibodies of the disclosure (including variants and derivatives thereof as described herein), and fragments thereof.

The antibodies of the disclosure can be used to treat or inhibit cancer. In some embodiments, provided are methods for treating a cancer in a patient in need thereof. The method, in some embodiments, comprises administering to the patient an effective amount of an antibody of the present disclosure. In some embodiments, at least one of the cancer cells (e.g., stromal cells) in the patient expresses, overexpress, or is induced to express CD47. Induction of PD-L1 expression, for instance, can be done by administration of a tumor vaccine or radiotherapy.

Tumors that express the CD47 protein include, but are not limited, to, those of bladder cancer, non-small cell lung cancer, renal cancer, breast cancer, urethral cancer, colorectal cancer, head and neck cancer, squamous cell cancer, Merkel cell carcinoma, gastrointestinal cancer, stomach cancer, oesophageal cancer, ovarian cancer, renal cancer, and small cell lung cancer. The presently disclosed antibodies can be used for treating any one or more such cancers.

Cellular therapies, such as chimeric antigen receptor (CAR) T-cell therapies, are also provided in the present disclosure. A suitable cell can be used, that is put in contact with an anti-CD47 antibody of the present disclosure (or alternatively engineered to express an anti-CD47 antibody of the present disclosure). Upon such contact or engineering, the cell can then be introduced to a cancer patient in need of a treatment. The cancer patient may have a cancer of any of the types as disclosed herein. The cell (e.g., T cell) can be, for instance, a tumor-infiltrating T lymphocyte, a CD4+ T cell, a CD8+ T cell, or the combination thereof, without limitation.

In some embodiments, the cell was isolated from the cancer patient him- or her-self. In some embodiments, the cell was provided by a donor or from a cell bank. When the cell is isolated from the cancer patient, undesired immune reactions can be minimized.

Additional diseases or conditions associated with increased cell survival, that may be treated, prevented, diagnosed and/or prognosed with the antibodies or variants, or derivatives thereof of the disclosure include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyo sarcoma, colon carcinoma, pancreatic cancer, breast cancer, thyroid cancer, endometrial cancer, melanoma, prostate cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma and retinoblastoma.

It has been shown that interactions between endothelial cell CD47 and leukocyte SIRPγ regulate T cell transendothelial migration (TEM) at sites of inflammation. CD47 knockout mice show reduced recruitment of blood T cells as well as neutrophils and monocytes in areas of inflammation. CD47 also functions as a marker of self on murine red blood cells which allows RBC to avoid phagocytosis. Red blood cells that lack CD47 are rapidly cleared from the bloodstream by macrophages, a process that is mediated by interaction with SIRPa.

In some embodiments, therefore, provided are compositions and methods for treating an autoimmune or inflammatory disease in a patient in need thereof, comprising administering to the patient an effective amount of the antibody or fragment thereof of the present disclosure.

Non-limiting examples of the autoimmune or inflammatory disease include Parkinson's disease, arthritis, rheumatoid arthritis, multiple sclerosis, psoriasis, psoriatic arthritis, Crohn's disease, inflammatory bowel disease, ulcerative colitis, lupus, systemic lupus erythematous, juvenile rheumatoid arthritis, juvenile idiopathic arthritis, Grave's disease, Hashimoto's thyroiditis, Addison's disease, celiac disease, dermatomyositis, multiple sclerosis, myasthenia gravis, pernicious anemia, Sjogren syndrome, type I diabetes, vasculitis, uveitis, atherosclerosis and ankylosing spondylitis. In one embodiment, the autoimmune or inflammatory disease is atherosclerosis.

Combination Therapies

In some embodiments, anti-CD47 antibodies or fragments thereof disclosed herein are administered in combination with an antineoplastic agent, an antiviral agent, antibacterial or antibiotic agent, and/or antifungal agents. Any of these agents known in the art may be administered in the compositions of the current disclosure.

In some embodiment, anti-CD47 antibodies or fragments thereof disclosed herein are administered in combination with a chemotherapeutic agent. Chemotherapeutic agents that may be administered with the compositions of the disclosure include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In some embodiment, anti-CD47 antibodies or fragments thereof disclosed herein are administered in combination with cytokines. Cytokines that may be administered with the compositions of the disclosure include, but are not limited to, IL-2, IL-3, IL-4, IL-5, IL-6, IL-7, IL-10, IL-12, IL-13, IL-15, anti-CD40, CD40L, and TNF-α.

In some embodiments, anti-CD47 antibodies or fragments thereof disclosed herein are administered in combination with other therapeutic or prophylactic regimens, such as, for example, radiation therapy.

In some embodiments, the anti-CD47 antibodies and compositions described herein may be used or combined with one or more additional therapeutic agents. The one or more therapeutic agents include, but are not limited to, an inhibitor of Abl, activated CDC kinase (ACK), adenosine A2B receptor (A2B), apoptosis signal-regulating kinase (ASK), Auroa kinase, Bruton's tyrosine kinase (BTK), BET-bromodomain (BRD) such as BRD4, c-Kit, c-Met, CDK-activating kinase (CAK), calmodulin-dependent protein kinase (CaMK), cyclin-dependent kinase (CDK), casein kinase (CK), discoidin domain receptor (DDR), epidermal growth factor receptors (EGFR), focal adhesion kinase (FAK), Flt-3, FYN, glycogen synthase kinase (GSK), HCK, histone deacetylase (HDAC), IKK such as IKKβε, isocitrate dehydrogenase (IDH) such as IDH1, Janus kinase (JAK), KDR, lymphocyte-specific protein tyrosine kinase (LCK), lysyl oxidase protein, lysyl oxidase-like protein (LOXL), LYN, matrix metalloprotease (MMP), MEK, mitogen-activated protein kinase (MAPK), NEK9, NPM-ALK, p38 kinase, platelet-derived growth factor (PDGF), phosphorylase kinase (PK), polo-like kinase (PLK), phosphatidylinositol 3-kinase (PI3K), protein kinase (PK) such as protein kinase A, B, and/or C, PYK, spleen tyrosine kinase (SYK), serine/threonine kinase TPL2, serine/threonine kinase STK, signal transduction and transcription (STAT), SRC, serine/threonine-protein kinase (TBK) such as TBK1, TIE, tyrosine kinase (TK), vascular endothelial growth factor receptor (VEGFR), YES, or any combination thereof.

The anti-CD47 antibodies of the present disclosure can be used, in some embodiments, together with an immune checkpoint inhibitor Immune checkpoints are molecules in the immune system that either turn up a signal (co-stimulatory molecules) or turn down a signal (co-inhibitory molecules). Many cancers protect themselves from the immune system by inhibiting the T cell signal through agonist for co-inhibitory molecules or antagonist for co-stimulatory molecules. An immune checkpoint agonist or antagonist can help stop such a protective mechanism by the cell cells. An immune checkpoint agonist or antagonistmay target any one or more of the following checkpoint molecules, PD-1, CTLA-4, LAG-3 (also known as CD223), CD28, CD122, 4-1BB (also known as CD137), TIM3, OX-40/OX40L, CD40/CD40L, LIGHT, ICOS/ICOSL, GITR/GITRL, TIGIT, CD27, VISTA, B7H3, B7H4, HEVM or BTLA (also known as CD272).

Programmed T cell death 1 (PD-1) is a trans-membrane protein found on the surface of T cells, which, when bound to programmed T cell death ligand 1 (PD-L1) on tumor cells, results in suppression of T cell activity and reduction of T cell-mediated cytotoxicity. Thus, PD-1 and PD-L1 are immune down-regulators or immune checkpoint "off switches". Example PD-1 inhibitor include, without limitation, nivolumab, (Opdivo™ anti-PD-1 antibody) (BMS-936558), pembrolizumab (Keytruda™ anti-PD-1 antibody), pidilizumab, AMP-224, MEDI0680 (AMP-514), PDR001, MPDL3280A, MEDI4736, BMS-936559 and MSB0010718C.

CTLA-4 is a protein receptor that downregulates the immune system. Non-limiting examples of CTLA-4 inhibitors include ipilimumab (Yervoy™ anti-CTLA-4 antibody) (also known as BMS-734016, MDX-010, MDX-101) and tremelimumab (formerly ticilimumab, CP-675,206).

Lymphocyte-activation gene 3 (LAG-3) is an immune checkpoint receptor on the cell surface works to suppress an immune response by action to Tregs as well as direct effects on CD8+ T cells. LAG-3 inhibitors include, without limitation, LAG525 and BMS-986016.

CD28 is constitutively expressed on almost all human CD4+ T cells and on around half of all CD8 T cells. prompts T cell expansion. Non-limiting examples of CD28 inhibitors include TGN1412.

CD122 increases the proliferation of CD8+ effector T cells. Non-limiting examples include NKTR-214.

4-1BB (also known as CD137) is involved in T-cell proliferation. CD137-mediated signaling is also known to protect T cells, and in particular, CD8+ T cells from activation-induced cell death. PF-05082566, Urelumab (BMS-663513) and lipocalin are example CD137 inhibitors.

For any of the above combination treatments, the anti-CD47 antibody can be administered concurrently or separately from the other anticancer agent. When administered separately, the anti-CD47 antibody can be administered before or after the other anticancer agent.

A specific dosage and treatment regimen for any particular patient will depend upon a variety of factors, including the particular antibodies, variant or derivative thereof used, the patient's age, body weight, general health, sex, and diet, and the time of administration, rate of excretion, drug combination, and the severity of the particular disease being treated. Judgment of such factors by medical caregivers is within the ordinary skill in the art. The amount will also depend on the individual patient to be treated, the route of administration, the type of formulation, the characteristics of the compound used, the severity of the disease, and the desired effect. The amount used can be determined by pharmacological and pharmacokinetic principles well known in the art.

Methods of administration of the antibodies, variants or include but are not limited to intradermal, intramuscular, intraperitoneal, intravenous, subcutaneous, intranasal, epidural, and oral routes. The antigen-binding polypeptides or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Thus, pharmaceutical compositions containing the antigen-binding polypeptides of the disclosure may be administered orally, rectally, parenterally, intracistemally, intravaginally, intraperitoneally, topically (as by powders, ointments, drops or transdermal patch), bucally, or as an oral or nasal spray.

The term "parenteral" as used herein refers to modes of administration which include intravenous, intramuscular, intraperitoneal, intrasternal, subcutaneous and intra-articular injection and infusion.

Administration can be systemic or local. In addition, it may be desirable to introduce the antibodies of the disclosure into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

It may be desirable to administer the antibodies polypeptides or compositions of the disclosure locally to the area in need of treatment; this may be achieved by, for example, and not by way of limitation, local infusion during surgery, topical application, e.g., in conjunction, with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the disclosure, care must be taken to use materials to which the protein does not absorb.

In some embodiments, the antigen-binding polypeptide or composition can be delivered in a controlled release system. For example, a pump may be used (see Sefton, 1987, *CRC Crit. Ref. Biomed. Eng.* 14:201; Buchwald et al., 1980, *Surgery* 88:507; Saudek et al., 1989, *N. Engl. J. Med.* 321:574). As another example, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); *Ranger and Peppas, J.,* 1983, *Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 71:105). In yet another example, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)). Some other non-limiting examples of controlled release systems are discussed in the review by Langer (1990, Science 249:1527-1533).

In some embodiments where the composition of the disclosure comprises a nucleic acid or polynucleotide encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see, e.g., Joliot et al., 1991, *Proc. Natl. Acad. Sci. USA* 88:1864-1868), etc. Alternatively, a nucleic acid can be introduced intracellularly and incorporated within host cell DNA for expression, by homologous recombination.

The amount of the antibodies of the disclosure which will be effective in the treatment, inhibition and prevention of an inflammatory, immune or malignant disease, disorder or condition can be determined by standard clinical techniques. In addition, in vitro assays may optionally be employed to help identify optimal dosage ranges. The precise dose to be employed in the formulation will also depend on the route of administration, and the seriousness of the disease, disorder or condition, and should be decided according to the judgment of the practitioner and each patient's circumstances. Effective doses may be extrapolated from dose-response curves derived from in vitro or animal model test systems.

As a general proposition, the dosage administered to a patient of the antigen-binding polypeptides of the present disclosure is typically 0.1 mg/kg to 100 mg/kg of the patient's body weight, between 0.1 mg/kg and 20 mg/kg of the patient's body weight, or 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the disclosure may be reduced by enhancing uptake and tissue penetration (e.g., into the brain) of the antibodies by modifications such as, for example, lipidation.

The methods for treating a malignant disease, condition or disorder comprising administration of an antibody, variant, or derivative thereof of the disclosure are typically tested in vitro, and then in vivo in an acceptable animal model, for the desired therapeutic or prophylactic activity, prior to use in humans. Suitable animal models, including transgenic animals, are well known to those of ordinary skill in the art. For example, in vitro assays to demonstrate the therapeutic utility of antigen-binding polypeptide described herein include the effect of an antigen-binding polypeptide on a cell line or a patient tissue sample. The effect of the antigen-binding polypeptide on the cell line and/or tissue sample can be determined utilizing techniques known to those of skill in the art, such as the assays disclosed elsewhere herein. In accordance with the disclosure, in vitro assays which can be used to determine whether administration of a specific antigen-binding polypeptide is indicated, include in vitro cell culture assays in which a patient tissue sample is grown in culture, and exposed to or otherwise administered a compound, and the effect of such compound upon the tissue sample is observed.

Various delivery systems are known and can be used to administer an antibody of the disclosure or a polynucleotide encoding an antibody of the disclosure, e.g., encapsulation in liposomes, microparticles, microcapsules, recombinant cells capable of expressing the compound, receptor-mediated endocytosis (see, e.g., Wu and Wu, 1987, *J. Biol. Chem.* 262:4429-4432), construction of a nucleic acid as part of a retroviral or other vector, etc.

Diagnostic Methods

Over-expression of CD47 is observed in some tumor samples, and patients having CD47-over-expressing cells are likely responsive to treatments with the anti-CD47 antibodies of the present disclosure. Accordingly, the antibodies of the present disclosure can also be used for diagnostic and prognostic purposes.

A sample that preferably includes a cell can be obtained from a patient, which can be a cancer patient or a patient desiring diagnosis. The cell be a cell of a tumor tissue or a tumor block, a blood sample, a urine sample or any sample from the patient. Upon optional pre-treatment of the sample, the sample can be incubated with an antibody of the present disclosure under conditions allowing the antibody to interact with a CD47 protein potentially present in the sample. Methods such as ELISA can be used, taking advantage of the anti-CD47 antibody, to detect the presence of CD47 protein in a sample.

Presence of the CD47 protein in the sample (optionally with the amount or concentration) can be used for diagnosis of cancer, as an indication that the patient is suitable for a treatment with an anti-CD47 antibody, or as an indication that the patient has (or has not) responded to a cancer treatment. For a prognostic method, the detection can be done at once, twice or more, at certain stages, upon initiation of a cancer treatment to indicate the progress of the treatment.

Compositions

The present disclosure also provides pharmaceutical compositions. Such compositions comprise an effective amount of an anti-CD47 antibody or a fragment thereof disclosed herein, and a pharmaceutically acceptable carrier. In some embodiments, the composition further includes a second anticancer agent (e.g., an immune checkpoint inhibitor).

In a some embodiments, the term "pharmaceutically acceptable" means approved by a regulatory agency of the Federal or a state government or listed in the U.S. Pharmacopeia or other generally recognized pharmacopeia for use in animals, and more particularly in humans. A "pharmaceutically acceptable carrier" is generally a non-toxic solid, semisolid or liquid filler, diluent, encapsulating material or formulation auxiliary of any type.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose are also envisioned. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences by E. W. Martin, incorporated herein by reference. Such compositions will contain a therapeutically effective amount of the antigen-binding polypeptide, preferably in purified form, together with a suitable amount of carrier so as to provide the form for proper administration to the patient. The formulation should suit the mode of administration. The parental preparation can be enclosed in ampoules, disposable syringes or multiple dose vials made of glass or plastic.

In some embodiments, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

EXAMPLES

Example 1: Generation of Mouse Monoclonal Antibodies Against Human CD47

Anti-human-CD47 mouse monoclonal antibodies were generated using the hybridoma technology.

Antigen: human CD47-Fc protein (Sino Biological, Cat #12283-H02H).

Immunization: To generate mouse monoclonal antibodies to human CD47, 6-8 week female BALB/c mice were immunized with CD47-Fc protein. Post 4 rounds of immunization, the serum of immunized mice was subjected to the antibody titer evaluation by ELISA. Briefly, microtiter plates were coated with human CD47 protein at 10 µg/ml in ELISA coating buffer, 100 µl/well at 4° C. room temperature (RT) overnight, then blocked with 200 µl/well of 5% non-fat milk. Dilutions of serum from immunized mice were added to each well and incubated for 1-2 hours at 37° C. The plates were washed with PBS/Tween and then incubate with anti-mouse IgG antibody conjugated with Horse Radish Peroxidase (HRP) for 1 hour at 37° C. After washing, the plates were developed with TMB substrate and analyzed by spectrophotometer at OD 450 nm. Mice with sufficient titers of anti-CD47 IgG were boosted with 40 µg human CD47-Fc protein at Day 42 post-immunization.

Immunized library construction: The phage library was constructed using phagemid vectors which consisted of the antibody gene fragments that were amplified from spleens of CD47 immunized mice. The antibody format is Fab fragment in phage display library. Two immunized libraries were generated from No. 3 and No. 5 mice respectively. The library size was $1.2 \times 10^8$ and the sequence diversity was analyzed as follows. For the 10 clones picked up from each library and further sequenced. More than 90% sequence showed enough diversity in CDRs for these two libraries.

Phage Panning and Clone Selection: CD47 is a 50 kDa membrane receptor that has an extracellular N-terminal IgV domain, five transmembrane domains, and a short C-terminal intracellular tail. Human CD47-IgV domain protein conjugated with human Fc or Biotinylated human CD47-IgV domain protein (Sino Biological, Cat #12283-H02H) was used as antigen for phage library panning.

Phage library solution panning against human CD47-Fc protein: Biotin-labeled CD47-Fc protein was first incubated with streptavidin-Dynabeads. The phage libraries were incubated with Biotin-labeled CD47 coated Dynabeads and washed in Kingfisher magnetic bead purification system. The bound phages were eluted with Trypsin. The resulting phage is out-put 1. The bound phages were incubated with SS320 cells and plated on 2YT plates for next round of panning screening. There was a total of 3-round of panning screening. The phage ELISA of output1, output2 and output3 showed enriched CD47 binders after three rounds of screening.

Single clones were picked from output 2 and output 3 phages. The *E. coli* supernatants of these clones were subjected to antigen binding ELISA. The clones that showed good binding potency were selected for subsequent sequencing. Nine unique sequences were identified.

The nine sequences were cloned into PcDNA 3.4 vector and expressed in 293 T cells. The monoclonal antibodies were purified from the culture supernatant by protein G. The purified antibodies were subjected to ELISA binding evaluation on CD47-His protein. As shown in FIG. 1, G08 and H06 clones showed dose dependent binding to CD47 antigen.

TABLE 4

G08 and H06 variable sequences

| Name | Sequence | SEQ ID NO: |
|---|---|---|
| G08 VH | QIQLQQSGPELVKPGASVKISCKASGDTFTDYY INWVKQKPGQGLEWIGWIYTGSGNTKYNEKFKG KTTLTVDTSSSTAYMQLNSLTSEDTAVYFCARY NPLITAVVPDYWGQGTTLTVSS | 11 |

TABLE 4-continued

G08 and H06 variable sequences

| Name | Sequence | SEQ ID NO: |
|---|---|---|
| G08 VL | DIVMSQSPSSLAVSVGEKVTMSCKSSQSLLYSS NQKNYLAWYQQKPGQSPKLLIYWASTRESGVPD RFTGSGSGTDFTLTISSVKAEDLAVYYCQQYYS YPPTFGGGTKLEIK | 12 |
| H06 VH | QIQLQQSGPELVKPGASVKISCKASGYTFTDYY INWVKQKPGQGPEWIGWIYPGSANTKYSEKVKG KATLTVDTSSTTAYMQLSSLTSDDTAVYFCTRN DPLITAVVPDYWGQGTTLTVSS | 13 |
| H06 VL | DIVMSQSPSSLAVSVGEKVTMSCRSSQSRLYSS NQKNYLAWYQQKPGQSPKLLIYWASTRESGVPD RFTGSGSGTDFTLTISSVKAEDLAVYYCQQYYN YPPTFGGGTKLEIK | 14 |

TABLE 5

G08 and H06 CDR sequences

| | Sequence | SEQ ID NO: |
|---|---|---|
| G08 | | |
| CDRH1 | DYYIN | 1 |
| CDRH2 | WIYTGSGNTKYNEKFKG | 2 |
| CDRH3 | YNPLITAVVPDY | 3 |
| CDRL1 | KSSQSLLYSSNQKNYLA | 4 |
| CDRL2 | WASTRES | 5 |
| CDRL3 | QQYYSYPPT | 6 |
| H06 | | |
| CDRH1 | DYYIN | 1 |
| CDRH2 | WIYPGSANTKYSEKVKG | 7 |
| CDRH3 | NDPLITAVVPDY | 8 |
| CDRL1 | RSSQSRLYSSNQKNYLA | 9 |
| CDRL2 | WASTRES | 5 |
| CDRL3 | QQYYNYPPT | 10 |

Example 2: Blockade of CD47/SIRP-α Interaction by Mouse Monoclonal Antibodies Against Human CD47

To further evaluate the functions of the mouse anti-huCD47 mAbs on blocking SIRP-α interaction, the HTRF assay was employed. The interaction between Tag1-SIRP-α and Tag2-CD47 was detected by using anti-Tag1-Terbium (HTRF donor) and anti-Tag2-XL665 (HTRF acceptor). When the donor and acceptor antibodies were brought into close proximity due to SIRP-α and CD47 binding, excitation of the donor antibody triggered fluorescent resonance energy transfer (FRET) towards the acceptor antibody, which in turn emits specifically at 665 nm. This specific signal is directly proportional to the extent of CD47/SIRP-α interaction. Thus, a molecule blocking CD47/SIRP-α interaction would cause a reduction in HTRF signal.

Figure 2:
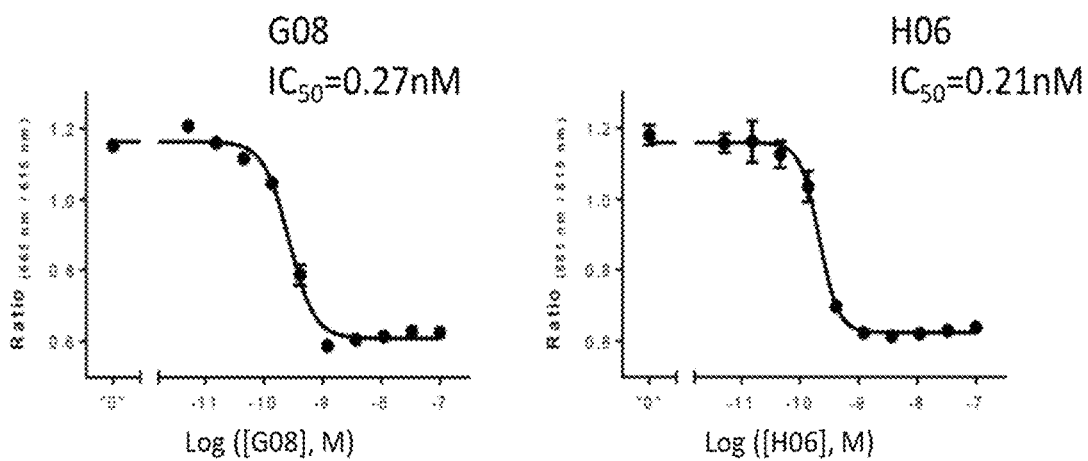
FIG. 2 shows that G08 and H06 antibodies block CD47/SIRP-α interaction in a dose-dependent manner.

G08 and H06 antibodies were evaluated for their activity to blocking the interaction of CD47 and SIRP-α. As shown in FIG. 2, both G08 and H06 antibodies can block the CD47/SIRP-α interaction in a dose-dependent manner.

Example 3: Humanization Design of G08 and H06 Clone

The mAb G08 and H06 variable region genes were employed to create a humanized monoclonal antibodies (mAb). First, the amino acid sequences of the VH and VK of mAb G08 and H06 were compared against the available database of human Ig gene sequences to find the overall best-matching human germline Ig gene sequences. For the light chain, the closest human match was the Vk1-4 gene, and for the heavy chain the closest human match was the VH1-2 gene.

Humanized variable domain sequences were then designed where the CDRL1, L2 and L3 were grafted onto framework sequences of the Vk1-4 gene, and the CDRH1, H2, and H3 onto framework sequences of the VH1-2 gene. A 3D model was then generated to determine if there were any framework positions where replacing the mouse amino acid to the human amino acid could affect binding and/or CDR conformation. In the case of the heavy chain, R and V in the framework was involved in back-mutations.

TABLE 6

G08 and H06 CDR sequences
(bold/italic indicates back mutations)

| | Sequence | SEQ ID NO: |
|---|---|---|
| G08 | | |
| VH mouse | QIQLQQSGPELVKPGASVKISCKASGDTFT DYYINWVKQPGQGLEWIGWIYTGSGNTKY NEKFKGKTTLTVDTSSSTAYMQLNSLTSED TAVYFCARYNPLITAVVPDYWGQGTTLTVS S | 11 |
| VH CDR grafting | QVQLVQSGAEVVKKPGASVKVSCKASGDTFT DYYINWVRQAPGQGLEWMGWIYTGSGNTKY NEKFKGRVTMTRDTSISTAYMELSRLRSDD TAVYYCARYNPLITAVVPDYWGQGTTVTVS S | 15 |
| VH CDRG-BM | QIQLVQSGAEVKKPGASVKVSCKASGDTFT DYYINWVRQAPGQGLEWMGWIYTGSGNTKY NEKFKGRVTMTVDTSISTAYMELSRLRSDD TAVYYCARYNPLITAVVPDYWGQGTTVTVS S | 16 |
| VL mouse | DIVMSQSPSSLAVSVGEKVTMSCKSSQSLL YSSNQKNYLAWYQQKPGQSPKLLIYWASTR ESGVPDRFTGSGSGTDFTLTISSVKAEDLA VYYCQQYYSYPPTFGGGTKLEIK | 12 |
| VL CDR grafting | DIVMTQSPDSLAVSLGERATINCKSSQSLL YSSNQKNYLAWYQQKPGQPPKLLIYWASTR ESGVPDRFSGSGSGTDFTLTISSLQAEDVA VYYCQQYYSYPPTFGGGTKVEIK | 17 |
| H06 | | |
| VH mouse | QIQLQQSGPELVKPGASVKISCKASGYTFT DYYINWVKQPGQGPEWIGWIYPGSANTKY SEKVKGKATLTVDTSSTTAYMQLSSLTSDD TAVYFCTRNDPLITAVVPDYWGQGTTLTVS S | 13 |

TABLE 6-continued

G08 and H06 CDR sequences
(bold/italic indicates back mutations)

| | Sequence | SEQ ID NO: |
|---|---|---|
| VH CDR grafting | QVQLVQSGAEVKKPGASVKVSCKASGYTFT DYYINWVRQAPGQGLEWMGWIYPGSANTKY SEKVKGRVTMTRDTSISTAYMELSRLRSDD TAVYYCARNDPLITAVVPDYWGQGTTVTVS S | 18 |
| VH CDRG-BM | QIQLVQSGAEVKKPGASVKVSCKASGYTFT DYYINWVRQAPGQGLEWMGWIYPGSANTKY SEKVKGRVTMTVDTSITTAYMELSRLRS DDTAVYYCTRNDPLITAVVPDYWGQGTTV TVSS | 19 |
| VL mouse | DIVMSQSPSSLAVSVGEKVTMSCRSSQSRL YSSNQKNYLAWYQQKPGQSPKLLIYWASTR ESGVPDRFTGSGSGTDFTLTISSVKAEDLA VYYCQQYYNYPPTFGGGTKLEIK | 14 |
| VL CDR grafting | DIVMTQSPDSLAVSLGERATINCRSSQSRL YSSNQKNYLAWYQQKPGQPPKLLIYWASTR ESGVPDRFSGSGSGTDFTLTISSLQAEDVA VYYCQQYYNYPPTFGGGTKVEIK | 20 |

Figure 3:
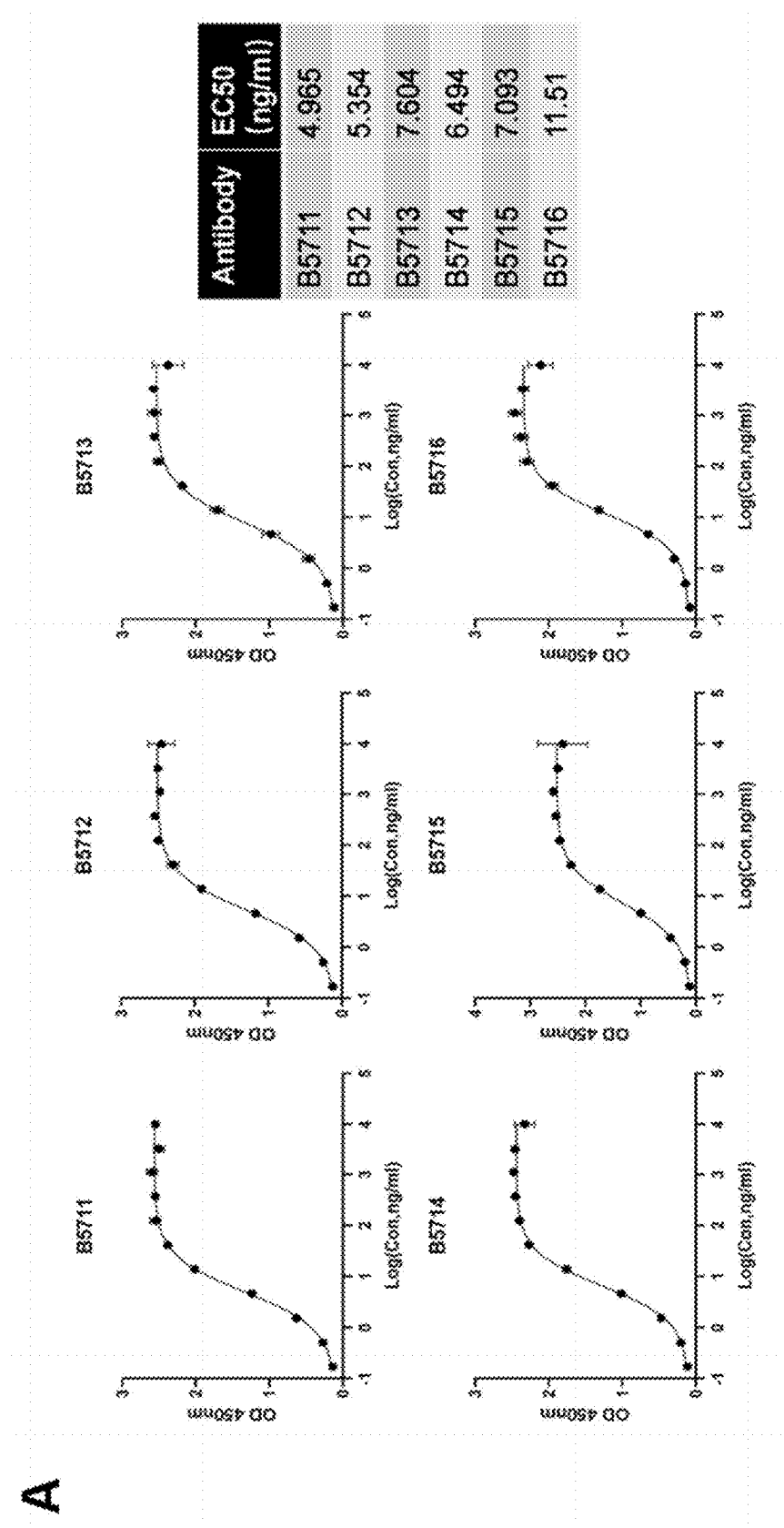
FIG. 3 shows humanized antibodies B5711, B5712, B5713, B5714, B5715, and B5716 bind to human CD47(A) and cynomolgus CD47 (B) in a dose-dependent manner.
Figure 3:
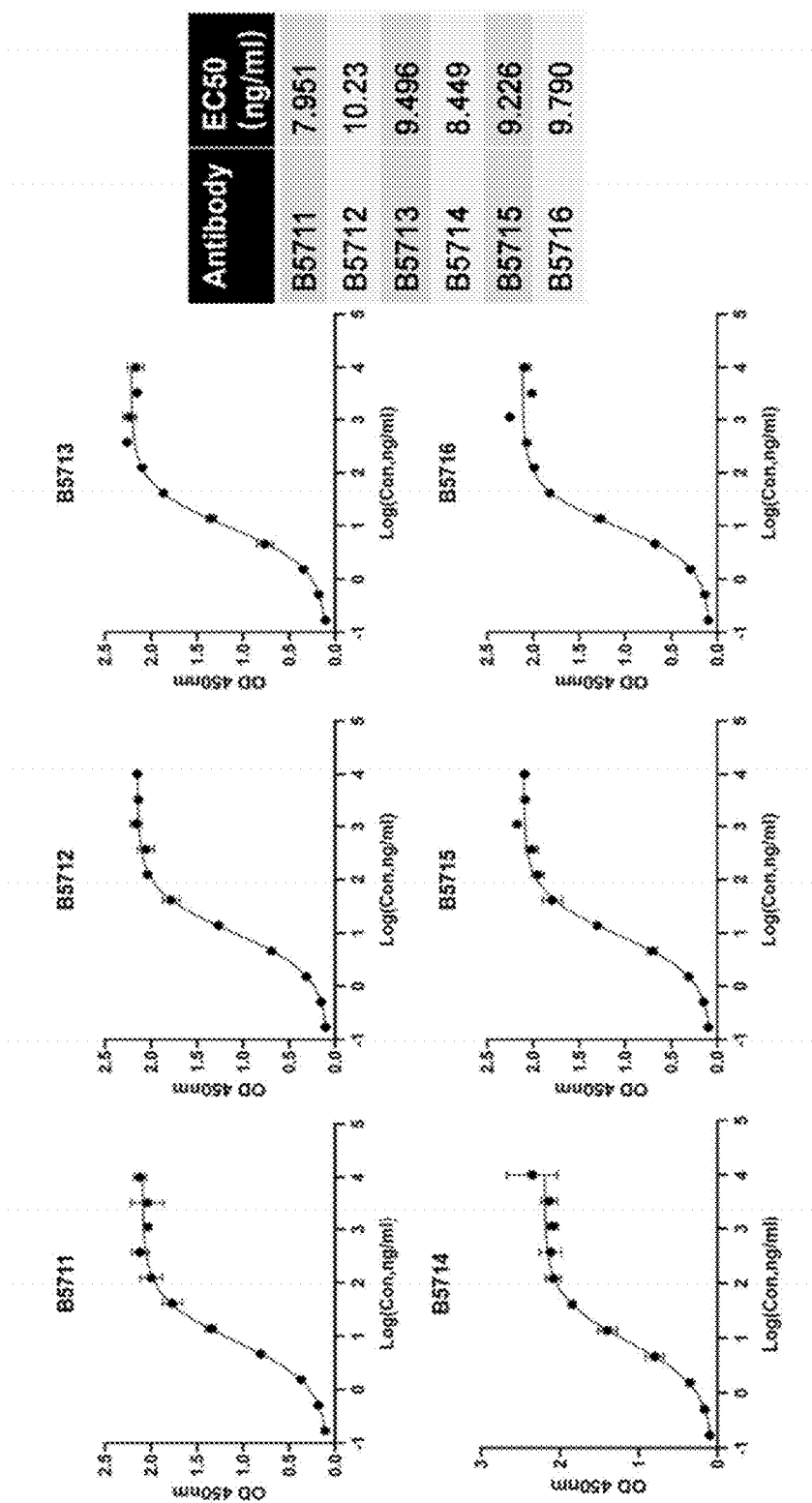

The gene was cloned in pcDNA 3.4 vector and transfected into 293F cells. The humanized antibodies were produced according to Table 7. The antibodies were purified from the culture supernatant by protein G. The purified antibodies were subjected to ELISA binding evaluation on both human CD47-His protein and cyno CD47-His protein. As show in FIG. 3, all antibodies showed dose dependent binding to both human CD47 and cyno CD47 proteins.

TABLE 7

Design of humanized CD47 antibodies

| Antibody Name | VH | VL |
|---|---|---|
| B5711 | G08 VH mouse | G08 VL mouse |
| B5712 | G08 VH CDR grafting | G08 VL CDR grafting |
| B5713 | G08 VH CDRG-BM | G08 VL CDR grafting |
| B5714 | H06 VH mouse | H06 VL mouse |
| B5715 | H06 VH CDR grafting | H06 VL CDR grafting |
| B5716 | H06 VH CDRG-BM | H06 VL CDR grafting |

Example 4: Blockade of CD47/SIRP-α Interaction by Humanized Monoclonal Antibodies Against Human CD47

To evaluate the activities of humanized anti-huCD47 mAbs on blocking SIRP-α interaction, the HTRF assay was employed. The interaction between Tag1-SIRP-α and Tag2-CD47 was detected by using anti-Tag1-Terbium (HTRF donor) and anti-Tag2-XL665 (HTRF acceptor). When the donor and acceptor antibodies were brought into close proximity due to SIRP-α and CD47 binding, excitation of the donor antibody triggers fluorescent resonance energy transfer (FRET) towards the acceptor antibody, which in turn emitted specifically at 665 nm. This specific signal is directly proportional to the extent of CD47/SIRP-α interaction. Thus, a molecule blocking CD47/SIRP-α interaction would cause a reduction in HTRF signal.

Figure 4:
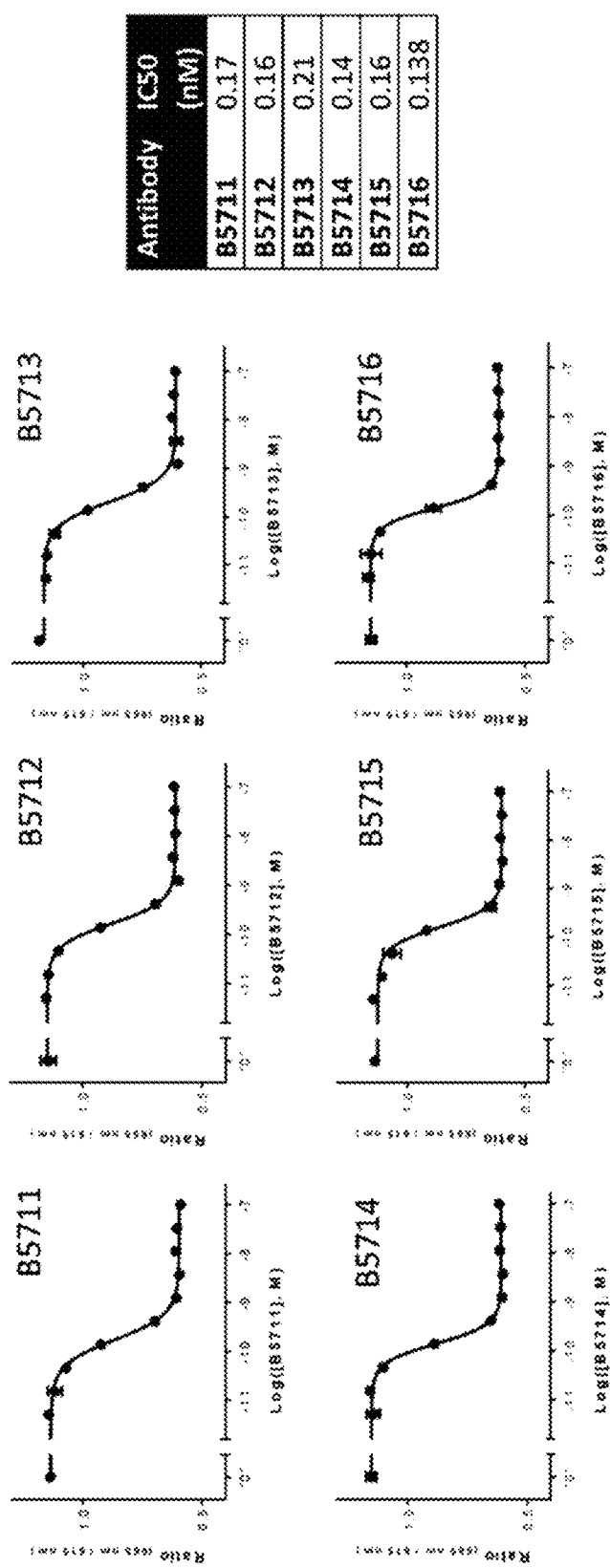
FIG. 4 shows that humanized antibodies B5711, B5712, B5713, B5714, B5715, and B5716 block CD47/SIRP-α interaction in a dose-dependent manner.

Anti-CD47 antibodies B5711, B5712, B5713, B5714, B5715, and B5716 were evaluated on their activities in blocking the interaction of CD47 and SIRP-α. As shown in FIG. 4, all these antibodies can block the CD47/SIRP-α interaction in a dose-dependent manner.

Example 5: RBC-Sparing Property in RBC Agglutination Assay

Figure 5:
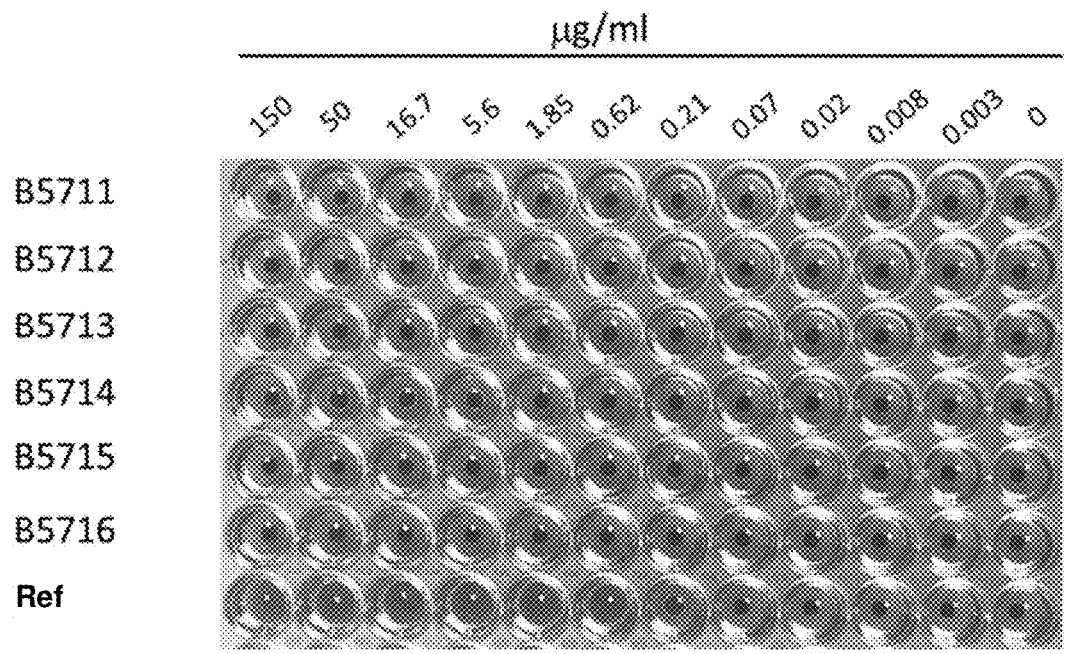
FIG. 5 shows red blood cell (RBC)-sparing property of anti-CD47 antibodies in a RBC Agglutination Assay.

Human red blood cells (RBCs) were diluted to 10% in PBS and incubated at 37° C. for 2 hours with a titration of CD47 antibodies in a round bottom 96-well plate. Evidence of hemagglutination is demonstrated by the presence of non-settled RBCs, appearing as a haze compared to a punctuate red dot of non-hemagglutinated RBCs (see FIG. 5).

Figure 6:
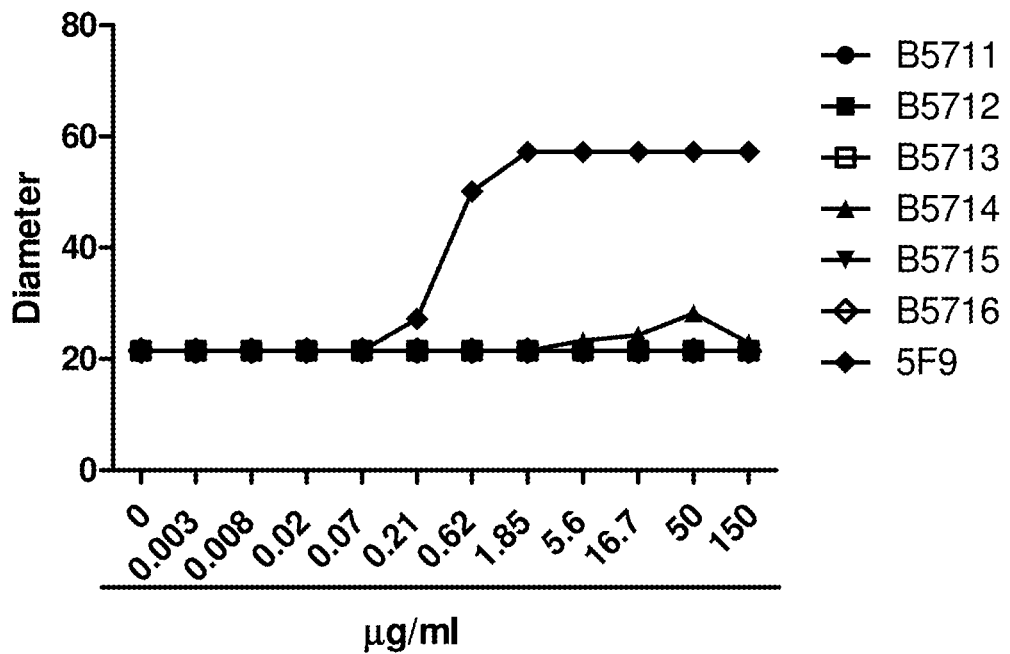
FIG. 6 is a plot showing quantitation of the RBC Agglutination assay of FIG. 3.

FIG. 6 shows the quantitation of the hemagglutination assay, denoted "agglutination index" determined by quantitating the area of the RBC pellet in the presence of the antibody, normalized to that of IgG control. While a known CD47 antibody Hu5F9-G4 (5F9) showed significant RBC agglutination at a concentration of or higher than 0.21 µg/mL, the new CD47 antibodies (B5711 to B5716) resulted in essentially no RBC agglutination at the tested concentrations up to 150 µg/mL.

Example 6: Full Kinetic Affinity of Humanized Antibodies by Biacore®

To explore the binding kinetics of the humanized antibody, this example performed the affinity ranking using biacore. B5711, B5712, B5713, B5714, B5715 and B5716 mAbs were captured using protein A chip. 5 nM of human CD47-his tag protein was injected over captured antibodies for 120s at a flow rate of 30 µL/min. The antigen was allowed to dissociate for 130s. As shown in Table 8, B5712, B5713, B5715, and B5716 show excellent affinity, which are comparable to the chimeric antibodies.

TABLE 8

Affinity ranking of humanized antibodies

| Antibody | CD47 his | | |
|---|---|---|---|
| | Ka(1/Ms) | kd (1/s) | KD (M) |
| B5711 | 4.673E+6 | 3.827E-3 | 8.189E-10 |
| B5712 | 2.146E+6 | 2.755E-3 | 1.284E-9 |
| B5713 | 3.530E+6 | 3.533E-3 | 1.001E-9 |
| B5714 | 1.889E+6 | 2.913E-3 | 1.542E-9 |
| B5715 | 2.386E+6 | 2.336E-3 | 9.791E-10 |
| B5716 | 8.259E+6 | 4.521E-3 | 5.474E-10 |

The binding of the humanized antibodies to recombinant CD47 protein (human CD47-his tag) was tested by BIACORE™ using a capture method. B5712 and B5715 mAbs were captured using protein A chip. A serial dilution of human CD47-his tag protein was injected over captured antibody for 120s at a flow rate of 30 µg/ml. The antigen was allowed to dissociate for 600s. All the experiments were carried out on a Biacore T200. Data analysis was carried out using Biacore T200 evaluation software and is shown in Table 9.

TABLE 9

Affinity by Biacore ®

| Antibody | CD47 his | | |
|---|---|---|---|
| | ka (1/Ms) | kd (1/s) | KD (M) |
| B5712 | 1.513E+6 | 1.282E-3 | 8.474E-10 |
| B5715 | 5.129E+5 | 2.871E-4 | 5.596E-10 |

Example 7: Study of Phagocytosis of Tumor Cells by Human Macrophage (MΦ)

PBMCs were isolated from human blood, and the monocytes were differentiated into macrophages for 6 days. The human tumor cell line HL-60 which endogenously expressed CD47 were chosen as target cells and labeled with PKH26, then added to MDMs at a ratio of 5:1 tumor cells per phagocyte and CD47 antibodies was added at various doses. After incubation for 1 hours, cells were resuspended by PBS, stained with macrophage marker CD11b antibody, and analyzed by flow cytometry. Phagocytosis was measured by gating on CD11b cells and then assessing the percent of PKH26+ cells.

Figure 7:
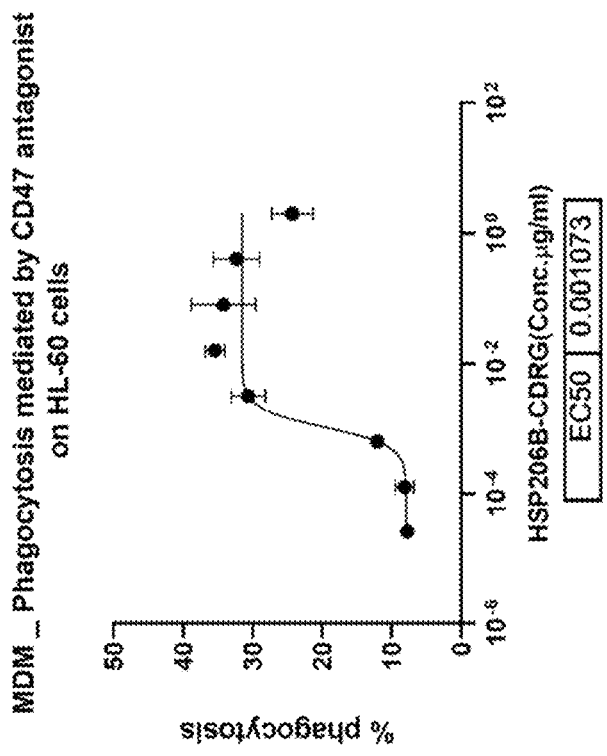
FIG. 7 is a plot showing that B5715 promoted phagocytosis of tumor cells by human macrophage (MΦ).
Figure 7:
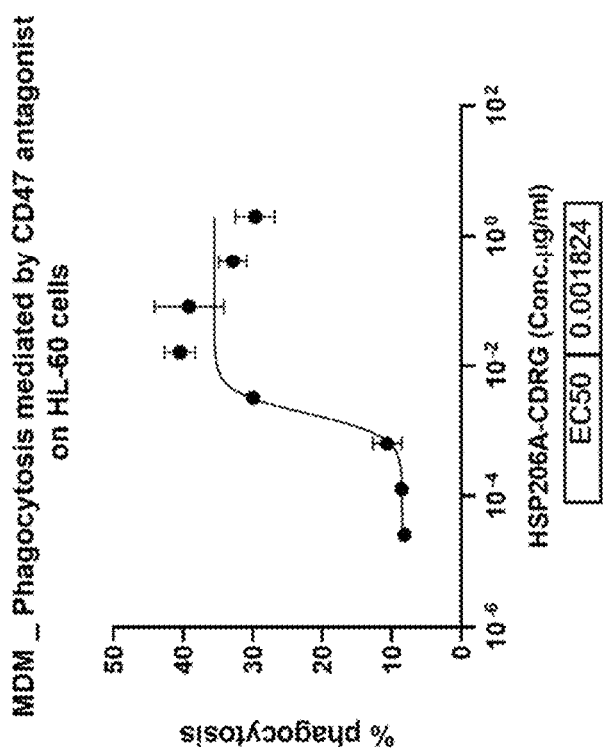

As shown in FIG. 7, B5712 (HSP206A-CDRG) and B5715(HSP206B-CDRG) can promote phagocytosis of tumor cells by human MΦ in a dose-dependent manner.

Example 8: Drug Efficacy Experiments in a Raji-Luc Lymphoma Mouse Model

This example tested the efficacies of humanized antibodies B5712 and B5715 in a Raji-Luc lymphoma mouse model.

Figure 8:
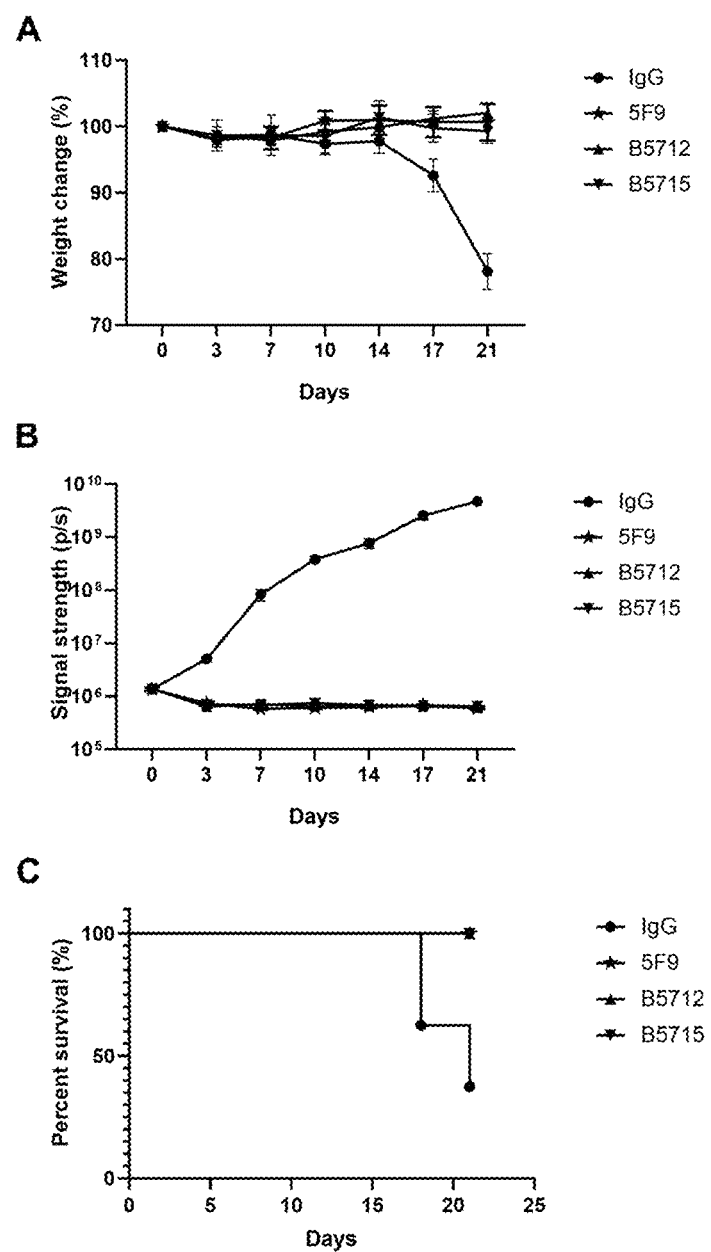
FIG. 8 show drug effects of B5712 and B5715 in animal models.

Raji-Luc cells resuspended in PBS were seeded into the tail vein of B-NDG mice at a concentration of $5 \times 10^5$ cells in a volume of 0.2 mL. On the 0th and 3rd days after injection, the tumor imaging signal value was measured using a small animal imager. When the average imaging signal intensity reached about $1 \times 10^6$ p/s, the appropriate animal was assigned to 4 experimental groups, 8 in each experimental group, according to the tumor imaging signal value and animal weight. Total human IgG, 5F9 (Hu5F9-G4), B5712 and B5715 were administered once every 3 day by intraperitoneal injection. The dose was calculated based on the experimental animal's body weight at 10 µg/g. Mice were weighed twice a week. The imaging signal map and signal intensity of murine tumor was obtained by using an IVIS Lumina LT twice a week. The results are shown in FIG. 8. Like 5F9, B5712 and B5715 exhibited potent in vivo efficacy in these mice in terms of weight loss (A), signal strength (B) and overall survival (C).

The present disclosure is not to be limited in scope by the specific embodiments described which are intended as single illustrations of individual aspects of the disclosure, and any compositions or methods which are functionally equivalent are within the scope of this disclosure. It will be apparent to those skilled in the art that various modifications and variations can be made in the methods and compositions of the present disclosure without departing from the spirit or scope of the disclosure. Thus, it is intended that the present disclosure cover the modifications and variations of this disclosure provided they come within the scope of the appended claims and their equivalents.

All publications and patent applications mentioned in this specification are herein incorporated by reference to the same extent as if each individual publication or patent application was specifically and individually indicated to be incorporated by reference

What is claimed is:

1. A method of treating cancer in a human patient having the cancer, comprising administering to the patient an effective amount of a monoclonal antibody or fragment thereof, wherein the antibody or fragment thereof has specificity to a human CD47 (Cluster of Differentiation 47) protein, and the antibody or the fragment comprises:
   (a) a VH CDR1 comprising the amino acid sequence of SEQ ID NO: 1;
   (b) a VH CDR2 comprising the amino acid sequence of SEQ ID NO: 7;
   (c) a VH CDR3 comprising the amino acid sequence of SEQ ID NO: 8;
   (d) a VL CDR1 comprising the amino acid sequence of SEQ ID NO: 9;
   (e) a VL CDR2 comprising the amino acid sequence of SEQ ID NO: 5; and
   (f) a VL CDR3 comprising the amino acid sequence of SEQ ID NO: 10, and wherein the fragment is selected from the group consisting of F(ab')$_2$, Fab', Fab, Fv, and scFv, wherein the cancer comprises cancer cells that express the human CD47 protein in the human patient.

2. The method of claim 1, wherein the antibody or fragment thereof comprises a heavy chain variable region comprising an amino acid sequence selected from the group consisting of SEQ ID NOs: 13 and 18-19, and a light chain variable region comprising an amino acid sequence selected from the group consisting of SEQ ID NOs: 14 and 20.

3. The method of claim 2, wherein the heavy chain variable region comprises the amino acid sequence of SEQ ID NO:18 or SEQ ID NO: 19, and the light chain variable region comprises the amino acid sequence of SEQ ID NO:20.

4. The method of claim 1, wherein the antibody is a humanized antibody.

5. The method of claim 1, wherein the cancer is a solid tumor.

6. The method of claim 1, wherein the cancer is a hematologic malignancy.

7. The method of claim 1, wherein the cancer is selected from the group consisting of bladder cancer, liver cancer, colon cancer, rectal cancer, endometrial cancer, leukemia, lymphoma, pancreatic cancer, small cell lung cancer, non-small cell lung cancer, breast cancer, urethral cancer, head and neck cancer, gastrointestinal cancer, stomach cancer, oesophageal cancer, ovarian cancer, renal cancer, melanoma, prostate cancer, thyroid cancer, and any combination thereof.

8. The method of claim 1, further comprising administering to the patient a second cancer therapeutic agent.

* * * * *

SEQUENCE LISTING

<160> NUMBER OF SEQ ID NOS: 20

<210> SEQ ID NO 1
<211> LENGTH: 5
<212> TYPE: PRT
<213> ORGANISM: Artificial Sequence
<220> FEATURE:
<223> OTHER INFORMATION: Synthetic

<400> SEQUENCE: 1

Asp Tyr Tyr Ile Asn
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic

<400> SEQUENCE: 2

Trp Ile Tyr Thr Gly Ser Gly Asn Thr Lys Tyr Asn Glu Lys Phe Lys
1               5                   10                  15

Gly

<210> SEQ ID NO 3
<211> LENGTH: 12
<212> TYPE: PRT
<213> ORGANISM: Artificial Sequence
<220> FEATURE:
<223> OTHER INFORMATION: Synthetic

<400> SEQUENCE: 3

Tyr Asn Pro Leu Ile Thr Ala Val Val Pro Asp Tyr
1               5                   10

<210> SEQ ID NO 4
<211> LENGTH: 17
<212> TYPE: PRT
<213> ORGANISM: Artificial Sequence
<220> FEATURE:
<223> OTHER INFORMATION: Synthetic

<400> SEQUENCE: 4

Lys Ser Ser Gln Ser Leu Leu Tyr Ser Asn Gln Lys Asn Tyr Leu
1               5                   10                  15

Ala

<210> SEQ ID NO 5
<211> LENGTH: 7
<212> TYPE: PRT
<213> ORGANISM: Artificial Sequence
<220> FEATURE:
<223> OTHER INFORMATION: Synthetic

<400> SEQUENCE: 5

Trp Ala Ser Thr Arg Glu Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic

```
<400> SEQUENCE: 6

Gln Gln Tyr Tyr Ser Tyr Pro Pro Thr
1               5

<210> SEQ ID NO 7
<211> LENGTH: 17
<212> TYPE: PRT
<213> ORGANISM: Artificial Sequence
<220> FEATURE:
<223> OTHER INFORMATION: Synthetic

<400> SEQUENCE: 7

Trp Ile Tyr Pro Gly Ser Ala Asn Thr Lys Tyr Ser Glu Lys Val Lys
1               5                   10                  15

Gly

<210> SEQ ID NO 8
<211> LENGTH: 12
<212> TYPE: PRT
<213> ORGANISM: Artificial Sequence
<220> FEATURE:
<223> OTHER INFORMATION: Synthetic

<400> SEQUENCE: 8

Asn Asp Pro Leu Ile Thr Ala Val Val Pro Asp Tyr
1               5                   10

<210> SEQ ID NO 9
<211> LENGTH: 17
<212> TYPE: PRT
<213> ORGANISM: Artificial Sequence
<220> FEATURE:
<223> OTHER INFORMATION: Synthetic

<400> SEQUENCE: 9

Arg Ser Ser Gln Ser Arg Leu Tyr Ser Ser Asn Gln Lys Asn Tyr Leu
1               5                   10                  15

Ala

<210> SEQ ID NO 10
<211> LENGTH: 9
<212> TYPE: PRT
<213> ORGANISM: Artificial Sequence
<220> FEATURE:
<223> OTHER INFORMATION: Synthetic

<400> SEQUENCE: 10

Gln Gln Tyr Tyr Asn Tyr Pro Pro Thr
1               5

<210> SEQ ID NO 11
<211> LENGTH: 121
<212> TYPE: PRT
<213> ORGANISM: Artificial Sequence
<220> FEATURE:
<223> OTHER INFORMATION: Synthetic

<400> SEQUENCE: 11

Gln Ile Gln Leu Gln Gln Ser Gly Pro Glu Leu Val Lys Pro Gly Ala
1               5                   10                  15

Ser Val Lys Ile Ser Cys Lys Ala Ser Gly Asp Thr Phe Thr Asp Tyr
                20                  25                  30

Tyr Ile Asn Trp Val Lys Gln Lys Pro Gly Gln Gly Leu Glu Trp Ile
            35                  40                  45
```

```
Gly Trp Ile Tyr Thr Gly Ser Gly Asn Thr Lys Tyr Asn Glu Lys Phe
         50                  55                  60

Lys Gly Lys Thr Thr Leu Thr Val Asp Thr Ser Ser Thr Ala Tyr
 65                  70                  75                  80

Met Gln Leu Asn Ser Leu Thr Ser Glu Asp Thr Ala Val Tyr Phe Cys
                 85                  90                  95

Ala Arg Tyr Asn Pro Leu Ile Thr Ala Val Val Pro Asp Tyr Trp Gly
                100                 105                 110

Gln Gly Thr Thr Leu Thr Val Ser Ser
                115                 120
```

<210> SEQ ID NO 12
<211> LENGTH: 113
<212> TYPE: PRT
<213> ORGANISM: Artificial Sequence
<220> FEATURE:
<223> OTHER INFORMATION: Synthetic

<400> SEQUENCE: 12

```
Asp Ile Val Met Ser Gln Ser Pro Ser Ser Leu Ala Val Ser Val Gly
  1               5                  10                  15

Glu Lys Val Thr Met Ser Cys Lys Ser Ser Gln Ser Leu Leu Tyr Ser
                 20                  25                  30

Ser Asn Gln Lys Asn Tyr Leu Ala Trp Tyr Gln Lys Pro Gly Gln
             35                  40                  45

Ser Pro Lys Leu Leu Ile Tyr Trp Ala Ser Thr Arg Glu Ser Gly Val
         50                  55                  60

Pro Asp Arg Phe Thr Gly Ser Gly Ser Gly Thr Asp Phe Thr Leu Thr
 65                  70                  75                  80

Ile Ser Ser Val Lys Ala Glu Asp Leu Ala Val Tyr Tyr Cys Gln Gln
                 85                  90                  95

Tyr Tyr Ser Tyr Pro Pro Thr Phe Gly Gly Gly Thr Lys Leu Glu Ile
                100                 105                 110

Lys
```

<210> SEQ ID NO 13
<211> LENGTH: 121
<212> TYPE: PRT
<213> ORGANISM: Artificial Sequence
<220> FEATURE:
<223> OTHER INFORMATION: Synthetic

<400> SEQUENCE: 13

```
Gln Ile Gln Leu Gln Gln Ser Gly Pro Glu Leu Val Lys Pro Gly Ala
  1               5                  10                  15

Ser Val Lys Ile Ser Cys Lys Ala Ser Gly Tyr Thr Phe Thr Asp Tyr
                 20                  25                  30

Tyr Ile Asn Trp Val Lys Gln Lys Pro Gly Gln Gly Pro Glu Trp Ile
             35                  40                  45

Gly Trp Ile Tyr Pro Gly Ser Ala Asn Thr Lys Tyr Ser Glu Lys Val
         50                  55                  60

Lys Gly Lys Ala Thr Leu Thr Val Asp Thr Ser Ser Thr Ala Tyr
 65                  70                  75                  80

Met Gln Leu Ser Ser Leu Thr Ser Asp Asp Thr Ala Val Tyr Phe Cys
                 85                  90                  95

Thr Arg Asn Asp Pro Leu Ile Thr Ala Val Val Pro Asp Tyr Trp Gly
                100                 105                 110
```

Gln Gly Thr Thr Leu Thr Val Ser Ser
        115                 120

<210> SEQ ID NO 14
<211> LENGTH: 113
<212> TYPE: PRT
<213> ORGANISM: Artificial Sequence
<220> FEATURE:
<223> OTHER INFORMATION: Synthetic

<400> SEQUENCE: 14

Asp Ile Val Met Ser Gln Ser Pro Ser Ser Leu Ala Val Ser Val Gly
1               5                   10                  15

Glu Lys Val Thr Met Ser Cys Arg Ser Ser Gln Ser Arg Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Asn Tyr Pro Pro Thr Phe Gly Gly Gly Thr Lys Leu Glu Ile
            100                 105                 110

Lys

<210> SEQ ID NO 15
<211> LENGTH: 121
<212> TYPE: PRT
<213> ORGANISM: Artificial Sequence
<220> FEATURE:
<223> OTHER INFORMATION: Synthetic

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Asp Thr Phe Thr Asp Tyr
            20                  25                  30

Tyr Ile Asn Trp Val Arg Gln Ala Pro Gly Gln Gly Leu Glu Trp Met
        35                  40                  45

Gly Trp Ile Tyr Thr Gly Ser Gly Asn Thr Lys Tyr Asn Glu Lys Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Tyr Asn Pro Leu Ile Thr Ala Val Val Pro Asp Tyr Trp Gly
            100                 105                 110

Gln Gly Thr Thr Val Thr Val Ser Ser
        115                 120

<210> SEQ ID NO 16
<211> LENGTH: 121
<212> TYPE: PRT
<213> ORGANISM: Artificial Sequence
<220> FEATURE:
<223> OTHER INFORMATION: Synthetic

<400> SEQUENCE: 16

Gln Ile Gln Leu Val Gln Ser Gly Ala Glu Val Lys Lys Pro Gly Ala
1               5                   10                  15

Ser Val Lys Val Ser Cys Lys Ala Ser Gly Asp Thr Phe Thr Asp Tyr
            20                  25                  30

Tyr Ile Asn Trp Val Arg Gln Ala Pro Gly Gln Gly Leu Glu Trp Met
        35                  40                  45

Gly Trp Ile Tyr Thr Gly Ser Gly Asn Thr Lys Tyr Asn Glu Lys Phe
    50                  55                  60

Lys Gly Arg Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Tyr Asn Pro Leu Ile Thr Ala Val Val Pro Tyr Trp Gly
            100                 105                 110

Gln Gly Thr Thr Val Thr Val Ser Ser
            115                 120

<210> SEQ ID NO 17
<211> LENGTH: 113
<212> TYPE: PRT
<213> ORGANISM: Artificial Sequence
<220> FEATURE:
<223> OTHER INFORMATION: Synthetic

<400> SEQUENCE: 17

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Tyr Pro Pro Thr Phe Gly Gly Gly Thr Lys Val Glu Ile
            100                 105                 110

Lys

<210> SEQ ID NO 18
<211> LENGTH: 121
<212> TYPE: PRT
<213> ORGANISM: Artificial Sequence
<220> FEATURE:
<223> OTHER INFORMATION: Synthetic

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile Asn Trp Val Arg Gln Ala Pro Gly Gln Gly Leu Glu Trp Met
        35                  40                  45

Gly Trp Ile Tyr Pro Gly Ser Ala Asn Thr Lys Tyr Ser Glu Lys Val

```
                50                  55                  60
Lys Gly Arg Val Thr Met Thr Arg Asp Thr Ser Ile Ser Thr Ala Tyr
 65                  70                  75                  80

Met Glu Leu Ser Arg Leu Arg Ser Asp Thr Ala Val Tyr Tyr Cys
                 85                  90                  95

Ala Arg Asn Asp Pro Leu Ile Thr Ala Val Val Pro Asp Tyr Trp Gly
                100                 105                 110

Gln Gly Thr Thr Val Thr Val Ser Ser
            115                 120

<210> SEQ ID NO 19
<211> LENGTH: 121
<212> TYPE: PRT
<213> ORGANISM: Artificial Sequence
<220> FEATURE:
<223> OTHER INFORMATION: Synthetic

<400> SEQUENCE: 19

Gln Ile Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
                20                  25                  30

Tyr Ile Asn Trp Val Arg Gln Ala Pro Gly Gln Gly Leu Glu Trp Met
             35                  40                  45

Gly Trp Ile Tyr Pro Gly Ser Ala Asn Thr Lys Tyr Ser Glu Lys Val
         50                  55                  60

Lys Gly Arg Val Thr Met Thr Val Asp Thr Ser Ile Thr Thr Ala Tyr
 65                  70                  75                  80

Met Glu Leu Ser Arg Leu Arg Ser Asp Thr Ala Val Tyr Tyr Cys
                 85                  90                  95

Thr Arg Asn Asp Pro Leu Ile Thr Ala Val Val Pro Asp Tyr Trp Gly
                100                 105                 110

Gln Gly Thr Thr Val Thr Val Ser Ser
            115                 120

<210> SEQ ID NO 20
<211> LENGTH: 113
<212> TYPE: PRT
<213> ORGANISM: Artificial Sequence
<220> FEATURE:
<223> OTHER INFORMATION: Synthetic

<400> SEQUENCE: 20

Asp Ile Val Met Thr Gln Ser Pro Asp Ser Leu Ala Val Ser Leu Gly
 1               5                  10                  15

Glu Arg Ala Thr Ile Asn Cys Arg Ser Ser Gln Ser Arg Leu Tyr Ser
                20                  25                  30

Ser Asn Gln Lys Asn Tyr Leu Ala Trp Tyr Gln Gln Lys Pro Gly Gln
             35                  40                  45

Pro Pro Lys Leu Leu Ile Tyr Trp Ala Ser Thr Arg Glu Ser Gly Val
         50                  55                  60

Pro Asp Arg Phe Ser Gly Ser Gly Ser Gly Thr Asp Phe Thr Leu Thr
 65                  70                  75                  80
```

```
Ile Ser Ser Leu Gln Ala Glu Asp Val Ala Val Tyr Tyr Cys Gln Gln
                85                  90                  95

Tyr Tyr Asn Tyr Pro Pro Thr Phe Gly Gly Gly Thr Lys Val Glu Ile
            100                 105                 110

Lys
```